(12) United States Patent
Marciacq et al.

(10) Patent No.: US 7,314,928 B2
(45) Date of Patent: Jan. 1, 2008

(54) PROCESS FOR MANUFACTURING MORPHOLINO-NUCLEOTIDES, AND USE THEREOF FOR THE ANALYSIS OF AND LABELLING OF NUCLEIC ACID SEQUENCES

(75) Inventors: Florence Marciacq, La Fare les Oliviers (FR); Sylvie Sauvaigo, Herbeys (FR); Jean-François Mouret, Coublevie (FR); Jean-Paul Issartel, St. Egreve (FR); Didier Molko, Tullins (FR)

(73) Assignees: Commissariat a l'Energie Atomique, Paris (FR); Centre National de la Recherche Scientifique, Paris Cedex (FR)

( * ) Notice: Subject to any disclaimer, the term of this patent is extended or adjusted under 35 U.S.C. 154(b) by 55 days.

(21) Appl. No.: 11/411,505

(22) Filed: Apr. 26, 2006

(65) Prior Publication Data

US 2006/0183204 A1   Aug. 17, 2006

Related U.S. Application Data

(60) Division of application No. 10/731,857, filed on Dec. 9, 2003, now Pat. No. 7,105,661, which is a continuation of application No. 09/914,221, filed as application No. PCT/FR00/00427 on Feb. 21, 2000, now Pat. No. 6,838,560.

(30) Foreign Application Priority Data

Feb. 22, 1999  (FR)  ................................... 99 02170
Sep. 27, 1999  (FR)  ................................... 99 12001

(51) Int. Cl.
*C07H 21/00* (2006.01)
*C07H 21/04* (2006.01)

(52) U.S. Cl. ................................. 536/25.32; 536/25.3

(58) Field of Classification Search ..................... None
See application file for complete search history.

(56) References Cited

U.S. PATENT DOCUMENTS

| 4,515,781 A | 5/1985 | Torrence et al. |
| 5,721,341 A | 2/1998 | Molko et al. |
| 5,849,482 A | 12/1998 | Meyer, Jr. et al. |
| 6,365,577 B1 | 4/2002 | Iversen |
| 6,838,560 B1 | 1/2005 | Marciacq et al. |

FOREIGN PATENT DOCUMENTS

| FR | 93 10864 | 9/1993 |
| WO | WO 95/07907 | 3/1995 |
| WO | WO 96/23807 | 8/1996 |

OTHER PUBLICATIONS

Rayford et al. The Journal of Biological Chemistry (1985), vol. 260, pp. 15708-15713.*

Agrawal, S., et al., "Efficient Methods for Attaching Non-Radioactive Labels to the 5' Ends of Synthetic Oligodeoxyribonucleotides", Nucleic Acids Research, vol. 14, No. 15: pp. 6227-6245; 1986.

Broker, T.R., et al., "Electron Microscopic Visualization of tRNA Genes with Ferritin-Avidin: Biotin Labels", Nucleic Acids Research, vol. 5, No. 2: pp. 363-385; 1978.

Girault, Isabelle, et al., "Use of Morpholinonucleotides to Conjugate Oxidized DNA Bases to Proteins", Bioconjugate Chem., vol. 7: pp. 445-450; 1996, XP002121979.

Hileman, R.E., et al., "Synthesis and Characterization of Conjugates Formed Between Periodate-Oxidized Ribonucleotides and Amine-Containing Fluorophores", Bioconjugate Chem., vol. 5, No. 5: pp. 436-444; 1994.

Lundwig, J., et al., "Rapid and Efficient Synthesis of Nucleoside 5'-O-(1-Thiotriphosphates), 5'-Triphosphates and 2', 3'-Cyclophosphorothioates Using 2-Chloro-4H-1,3,2-benzodioxaphosphorin-4-one", Journal of Organic Chemistry, vol. 54; pp. 631-635; 1989.

Prober, James M. et al., "A system for Rapid DNA Sequencing with Fluorescent Chain-Terminating Dideoxynucleotides", Science, vol. 238: pp. 336-341, Oct. 16, 1987.

Rayford, Richard, et al., "Reductive Alkylation with Oxidized Nucleotides: Use in Affinity Labeling or Affinity Chromatography", J. Biol. Chem, vol. 260, No. 29: pp. 15708-15713; 1985.

(Continued)

*Primary Examiner*—Patrick Lewis
(74) *Attorney, Agent, or Firm*—Hutchison Law Group PLLC

(57) ABSTRACT

The invention relates to the use of morpholino-nucleosides of formula:

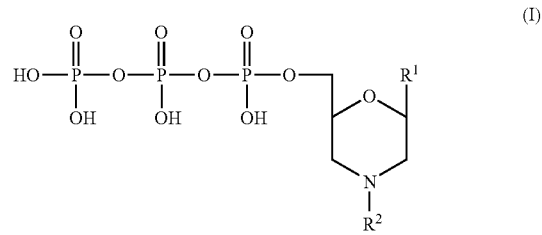

in which $R^1$ represents a nucleic base and $R^2$ represents a group corresponding to one of the following formulae:

—$(CH_2)_n$—$NH_2$ —$(CH_2)_n$—SH

—$(CH_2)_n$—COOH —$(CH_2)_n$—OH

—$(CH_2)_n$—NH—$R^3$ —$(CH_2)_n$—$SR^3$

—$(CH_2)_n$—CO—$R^3$ —$(CH_2)_n$—$OR^3$ in which n is an interger ranging from 1 to 12 and $R^3$ is a group derived from a label, from a protein, from an enzyme, from a fatty acid or from a peptide, as chain terminators in a process of DNA or RNA sequencing by the Sanger method, or for the labelling of DNA or RNA fragments.

8 Claims, 5 Drawing Sheets

OTHER PUBLICATIONS

Sanger, F., et al. "DNA Sequencing with Chain-Terminating Inhibitors", Proc. Natl. Acad. Sci. USA, vol. 74, No. 12: pp. 5463-5467; 1977, London.

Gregory, Martha R., et al., "Inactivation of Phosphofructokinase by Dialdehyde-ATP", Archives of Biochemistry and Biophysics, 196(1):199-208 (1979).

* cited by examiner

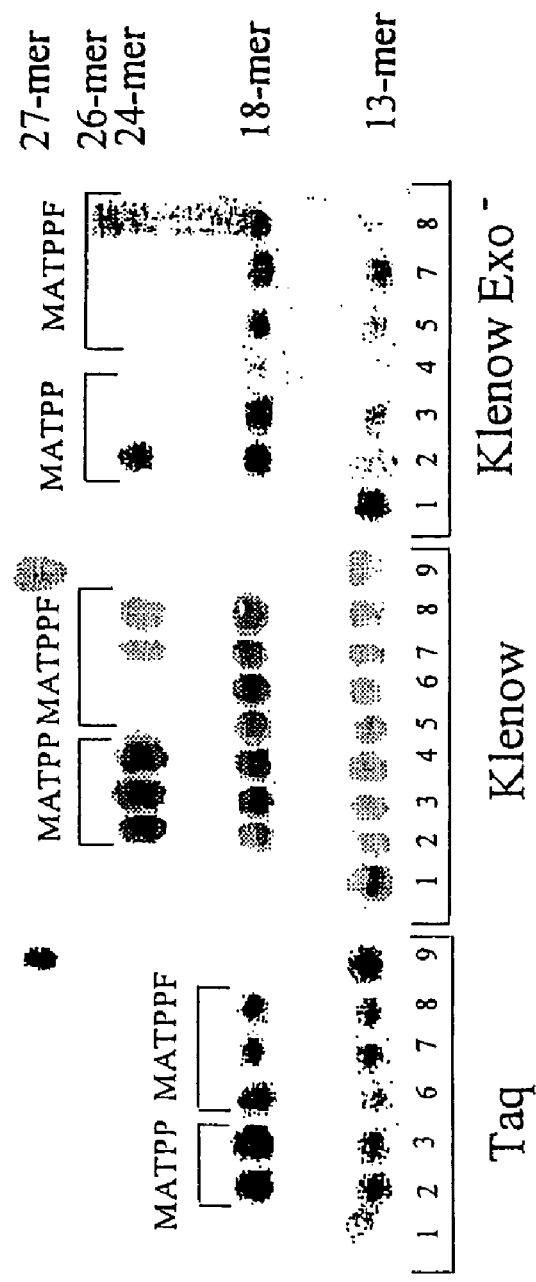
FIG. 4
FIG. 3
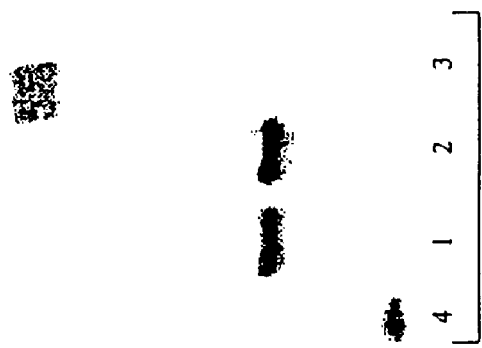

Figure 5
*Sequence to be analysed (polymerase template)*
3' HO-ApTpGpCpApApTpCpCpGpApTpGpApCpTpGpApGpCpCpApTpCpG 5'
(SEQ ID NO: 1)
*Primer*    +
5' TpApCpGpTpTpApGpGpC-OH 3' (SEQ ID NO: 2)
3' HO-ApTpGpCpApApTpCpCpGpApTpGpApCpTpGpApGpCpCpApTpCpG 5'
5' TpApCpGpTpTpApGpGpC-OH 3'
DNA Polymerase
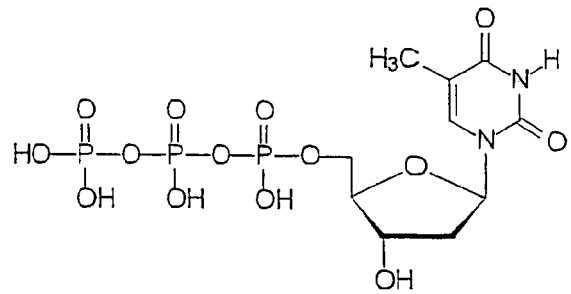
5' Thymidine triphosphate
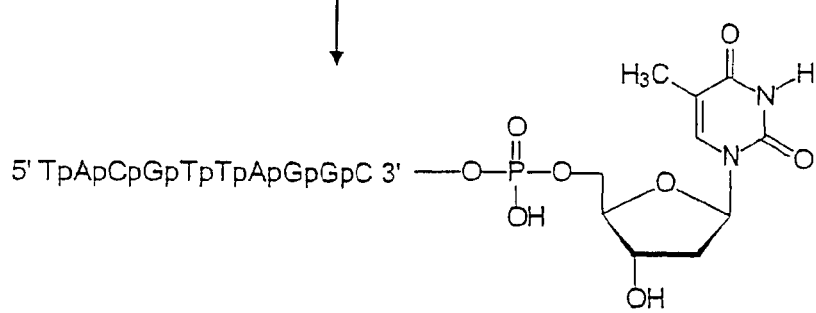
5' TpApCpGpTpTpApGpGpC 3'

Figure 6

*Sequence to be analysed (polymerase template)*
   3' HO-ApTpGpCpApApTpCpCpGpApTpGpApCpTpGpApGpCpCpApTpCpG 5'
   (SEQ ID NO: 1)

*Primer* +

5' TpApCpGpTpTpApGpGpC-OH 3' (SEQ ID NO: 2)

↓

3' HO-ApTpGpCpApApTpCpCpGpApTpGpApCpTpGpApGpCpCpApTpCpG 5'
   5' TpApCpGpTpTpApGpGpC-OH 3'

DNA Polymerase

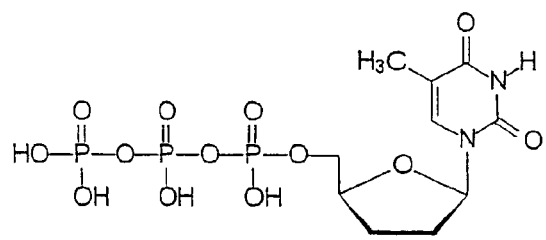

3'-deoxythymidine 5'-triphosphate

5' TpApCpGpTpTpApGpGpC 3' 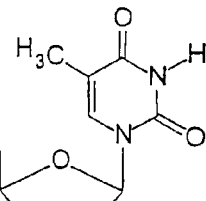

The newly synthesized chain no longer contains 3' OH
required to attach the next nucleotide

```
                               SEQUENCE LISTING

<160> NUMBER OF SEQ ID NOS: 13

<210> SEQ ID NO 1
<211> LENGTH: 25
<212> TYPE: DNA
<213> ORGANISM: Artificial Sequence
<220> FEATURE:
<223> OTHER INFORMATION: synthetic wrap

<400> SEQUENCE: 1
atgcaatccg atgactgagc catcg                                          25

<210> SEQ ID NO 2
<211> LENGTH: 10
<212> TYPE: DNA
<213> ORGANISM: Artificial Sequence
<220> FEATURE:
<223> OTHER INFORMATION: synthetic wrap

<400> SEQUENCE: 2
tacgttaggc                                                           10

<210> SEQ ID NO 3
<211> LENGTH: 22
<212> TYPE: DNA
<213> ORGANISM: Artificial Sequence
<220> FEATURE:
<223> OTHER INFORMATION: synthetic wrap

<400> SEQUENCE: 3
atgcattccg acctctgatc ag                                             22

<210> SEQ ID NO 4
<211> LENGTH: 11
<212> TYPE: DNA
<213> ORGANISM: Artificial Sequence
<220> FEATURE:
<223> OTHER INFORMATION: synthetic wrap

<400> SEQUENCE: 4
tacgtaaggc s                                                         11

<210> SEQ ID NO 5
<211> LENGTH: 18
<212> TYPE: DNA
<213> ORGANISM: Artificial Sequence
<220> FEATURE:
<223> OTHER INFORMATION: synthetic wrap

<400> SEQUENCE: 5
tacgtaaggc tggagacs                                                  18
```

<210> SEQ ID NO 6
<211> LENGTH: 21
<212> TYPE: DNA
<213> ORGANISM: Artificial Sequence
<220> FEATURE:
<223> OTHER INFORMATION: synthetic wrap

<400> SEQUENCE: 6
tacgtaaggc tggagactag s                                    21

<210> SEQ ID NO 7
<211> LENGTH: 27
<212> TYPE: DNA
<213> ORGANISM: Artificial Sequence
<220> FEATURE:
<223> OTHER INFORMATION: synthetic wrap

<400> SEQUENCE: 7
tgccaaccaa ccccacctca acctctg                              27

<210> SEQ ID NO 8
<211> LENGTH: 13
<212> TYPE: DNA
<213> ORGANISM: Artificial Sequence
<220> FEATURE:
<223> OTHER INFORMATION: synthetic wrap

<400> SEQUENCE: 8
acggttggtt ggg                                             13

<210> SEQ ID NO 9
<211> LENGTH: 15
<212> TYPE: DNA
<213> ORGANISM: Artificial Sequence
<220> FEATURE:
<223> OTHER INFORMATION: synthetic wrap

<400> SEQUENCE: 9
acggtttggg gtgga                                           15

<210> SEQ ID NO 10
<211> LENGTH: 24
<212> TYPE: DNA
<213> ORGANISM: Artificial Sequence
<220> FEATURE:
<223> OTHER INFORMATION: synthetic wrap

<400> SEQUENCE: 10
acggttggtt ggggtggagt tgga                                 24

<210> SEQ ID NO 11
<211> LENGTH: 26
<212> TYPE: DNA
<213> ORGANISM: Artificial Sequence
<220> FEATURE:
<223> OTHER INFORMATION: synthetic wrap

<400> SEQUENCE: 11
acggttggtt ggggtggagt tggaga                               26

<210> SEQ ID NO 12
<211> LENGTH: 27
<212> TYPE: DNA
<213> ORGANISM: Artificial Sequence
<220> FEATURE:
<223> OTHER INFORMATION: synthetic wrap

```
<400> SEQUENCE: 12
acggttggtt ggggtggagt tggagac                                    27

<210> SEQ ID NO 13
<211> LENGTH: 14
<212> TYPE: DNA
<213> ORGANISM: Artificial Sequence
<220> FEATURE:
<223> OTHER INFORMATION: synthetic wrap

<400> SEQUENCE: 13
acggttggtt gggg                                                  14
```

PROCESS FOR MANUFACTURING MORPHOLINO-NUCLEOTIDES, AND USE THEREOF FOR THE ANALYSIS OF AND LABELLING OF NUCLEIC ACID SEQUENCES

RELATED APPLICATIONS

This application is a divisional of application Ser. No. 10/731,857, filed Dec. 9, 2003 now U.S. Pat. No. 7,105,661, which is a continuation of application Ser. No. 09/914,221 filed Aug. 22, 2001 now U.S. Pat. No. 6,838,560, which is the National Stage of International Application No. PCT/FR00/00427, filed Feb. 21, 2000, which claims priority to application Ser. Nos. FR99/02170 and FR99/12001, filed on Feb. 22, 1999 and Sep. 27, 1999, respectively. The entire contents of these applications are hereby incorporated by reference herein.

TECHNICAL FIELD

The present invention relates to the manufacture of nucleic acid (DNA or RNA) fragments enzymatically extended with morpholino-nucleoside triphosphates. This elongation may be used for the analysis of nucleic acid sequences by incorporating these derivatives into nucleic acid chains, and also the enzymatic labelling and immobilization or detection of sequences.

These morpholino-nucleoside triphosphates may also be used with an additional molecule which may have various roles in many applications.

PRIOR ART

The method most widely used for analysing nucleic acid sequences is the enzymatic "chain termination" technique, developed by Sanger et al. in Proceedings of National Academy of Science, 74, 1977, p. 5463-5467 [1]. It is based on the properties of DNA-dependent DNA polymerases to create DNA polymers complementary to the sequence of a DNA strand serving as a template, from a mixture of natural nucleoside triphosphate monomers. The process consists, starting with the DNA strand to be analysed, in making a series of copies of the complementary strand by adding to the conventional reaction medium molecules known as "chain terminators" and then analysing the length of the newly formed strands to determine the base sequence of the template. The principle of the method is explained in Table 1 shown as FIG. 5.

TABLE 1

Sequence to be analysed (polymerase template)

3' HO-ApTpGpCpApApTpCpCpGpApTpGpApCpTpGpApGpCpCpApTpCpG 5'
(SEQ ID NO: 1)

Primer    +

5' TpApCpGpTpTpApGpGpC-OH 3' (SEQ ID NO: 2)

↓

3' HO-ApTpGpCpApApTpCpCpGpApTpGpApCpTpGpApGpCpCpApTpCpG 5'
   5' TpApCpGpTpTpApGpGpC-OH 3'

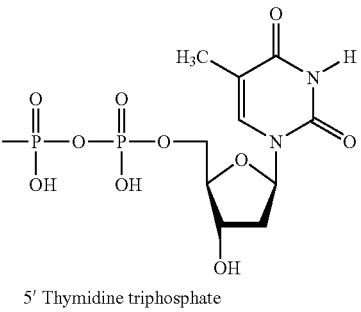

5' Thymidine triphosphate

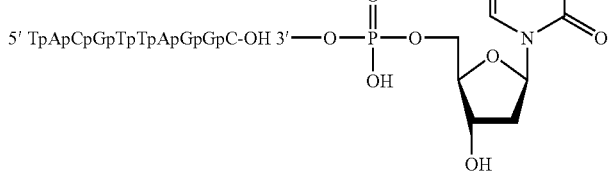

This Table 1 illustrates what happens when the DNA polymerase, a primer consisting of a small oligonucleotide, generally of less than 25 bases, and the mixture of the four natural nucleoside triphosphates are placed in contact with the DNA strand whose sequence it is desired to determine, which constitutes the template. The primer corresponds to the start of the complementary sequence of the DNA strand to be analysed. Starting with this primer, which interacts spontaneously with the complementary sequence of the DNA strand to be analysed (hybridization), the enzyme incorporates nucleotides complementary to the template to construct by elongation-polymerization a new DNA strand, which is a copy complementary to the said template. The new nucleotides are incorporated exclusively from the 3'-OH terminal end of the growing chain, sequentially and in compliance with the Watson & Crick rules of complementarity between bases. A thymine is incorporated into the newly formed strand by complementarity with an adenine present in the strand serving as the template, a guanine is incorporated in complementarity with a cytosine, and vice versa. If all the required compounds are supplied in unlimited amount, the enzyme catalyzes the polymerization of the strand formed until said strand represents the entire strand complementary to the matrix.

On the other hand, if a molecule which is recognized by the polymerase but which has no free 3'-OH terminal end is added to the reaction medium, each time this molecule is incorporated, the polymerization work of the enzyme will be interrupted because the chain can no longer grow on account of the absence of a site available to attach a new nucleotide (creation of interrupted newly-formed strands). This is illustrated in Table 2 shown as FIG. 6 with 3'-deoxythymidine 5'-triphosphate.

TABLE 2

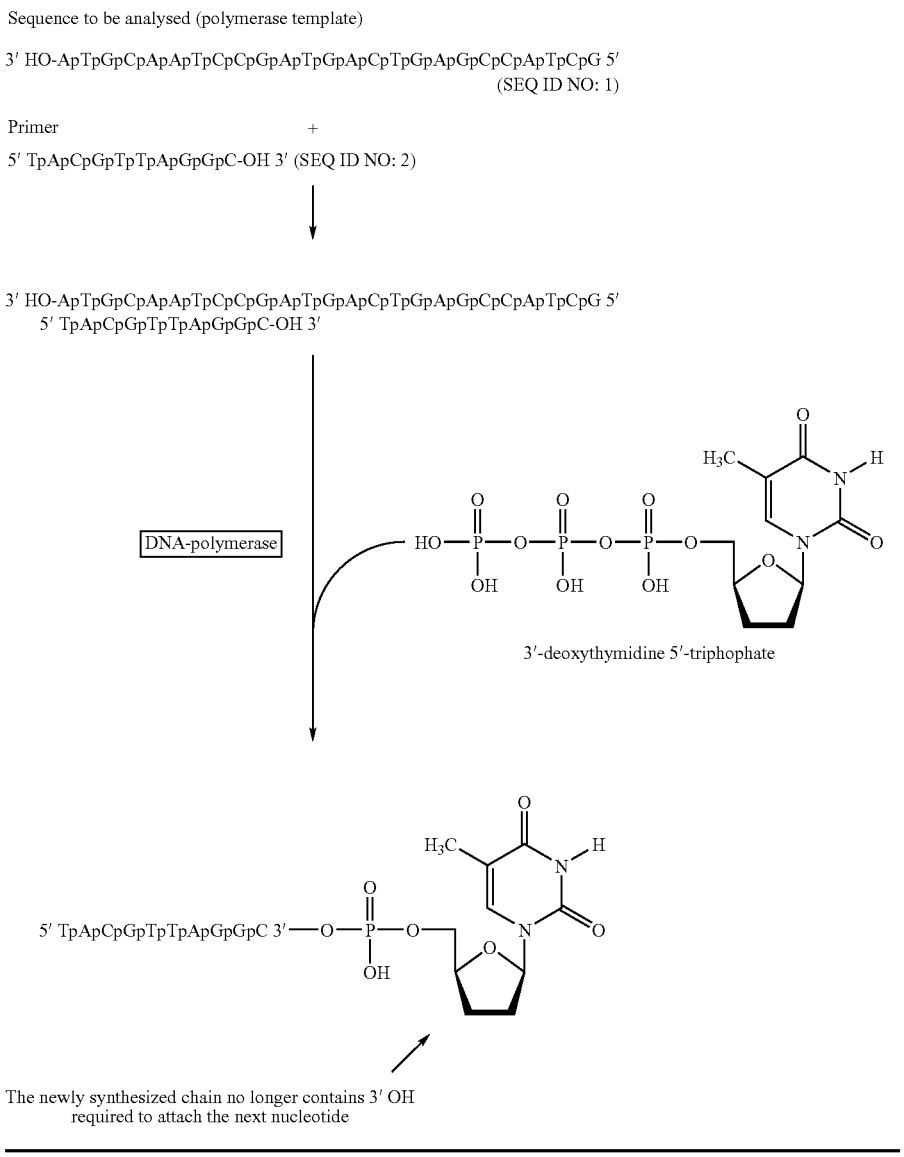

Using this thymidine derivative which will be referred to as a "T chain terminator" at a (inaudible) concentration, a series of DNA strands whose size is randomly fixed by the position of the adenines in the template is obtained for a given template. The result obtained is illustrated in Table 3. The sequence of the template is written in the first line and the sequence of the newly formed strands created with the T chain terminator (noted S) is written in the following lines.

TABLE 3

TEMPLATE

3' A T G C A T T C C G A C C T C T G A T C A G -5'
(SEQ ID NO: 3)

COPIES OF THE TEMPLATE

5'- S
5'- T A C G S
5'- T A C G T A A G G C S (SEQ ID NO: 4)
5'- T A C G T A A G G C T G G A G A C S
(SEQ ID NO: 5)
5'- T A C G T A A G G C T G G A G A C T A G S
(SEQ ID NO: 6)

In this example, the template comprises 5 adenines in the region which is detailed, and the DNA polymerase may thus produce 5 interrupted newly formed strands, of different lengths.

It then suffices to analyse this mixture by polyacrylamide gel electrophoresis in denaturing medium to determine the length of each of the strands obtained using the T chain terminator. The size of the interrupted newly formed strands makes it possible to deduce the position of the adenines on the matrix.

By repeating this experiment three times with A, G and C chain terminator products, respectively, four series of DNA fragments are obtained in total, the length of which fragments makes it possible to determine the entire sequence of the template strand.

The technique of RNA sequencing is based on the same principles, the difference being that the enzyme used is a reverse transcriptase (or RNA-dependent DNA polymerase).

The products most commonly used as chain terminators to stop the action of the DNA polymerases are 2',3'-dideoxy-nucleoside triphosphates of formula:

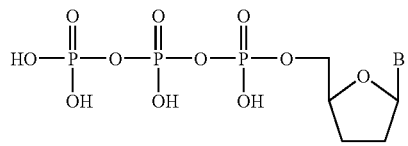

in which B represents one of the nucleic bases A, C, G or T, as described in document [1].

The structure of these products compared with that of the natural nucleoside triphosphates shows the absence of the hydroxyl function in the 3' position which serves as the position of attachment for the next nucleotide.

The chemical synthesis of 2',3'-dideoxynucleotides is performed according to a long and laborious protocol comprising three major steps. In the case of guanine, the first step of this process is the protection of the exocyclic amine function of the guanine and of the primary 5' hydroxyl function of the sugar. The 3' hydroxyl function is then deleted, by removal and then by reduction of the 2'-3' double bond generated. The final step is the preparation of the triphosphate derivative.

Other chain terminators have been described in document WO-A-96/23807 [2]. These are the 5'-triphosphates of arabinonucleosides, of 3'-fluoro-2',3'-dideoxynucleosides, 3'-azido-2',3'-dideoxynucleosides or 3'-amino-2',3'-dideoxynucleosides. These are also laborious to synthesize.

Originally in the Sanger method, the visualization of the DNA fragments synthesized was achieved by radioactive labelling with $^{32}P$ at the 5' end of the primer used to initiate the polymerization of the complementary strand. A modification was made by using primers bearing a fluorophore. This improvement has a bearing only on the ease of use, since it dispenses with the use of radioactive materials, but it is still necessary to carry out four sequencing reactions, each using a different polymerization terminator (A, G, T or C terminator).

A new landmark was passed with the use of sequence terminators bearing fluorophores on their nucleic base, as described by Prober et al. in Science, 238, 1987, pages 336-341 [3].

Under these conditions, the newly synthesized strands are no longer labelled before the sequencing reaction, but rather directly at the time of incorporation of the sequence terminator. By taking care to select a fluorophore with different optical properties for each DNA base, the experimental protocol was greatly simplified. Only one reaction is performed with the four terminators mixed together. As a result, starting with a single electrophoresis lane, the four nucleotides of the sequence are distinguished by virtue of the different emission wavelengths of the four terminators.

This simplification of the analysis protocol is not without drawbacks. Specifically, the fluorophores are grafted directly onto the base. This structural modification, located in the direct region of the sites of hydrogen bonding governing the recognition between the bases, results in a decrease in the recognition by the enzymes. To compensate for this, an increase in the concentration of the terminators is recommended, which leads to a very great consumption of the starting material having a very high added value. Furthermore, these molecules are still just as difficult to synthesize.

DESCRIPTION OF THE INVENTION

One subject of the present invention is in particular the use, in a sequencing process of this type, of chain terminators consisting of nucleotide triphosphate analogues which are easier to synthesize and which furthermore make it possible to carry out efficient labelling without modifying the nucleic bases.

Thus, one subject of the invention is a process for sequencing a nucleic acid (DNA or RNA) by the technique of enzymatic polymerization of the sequence complementary to this nucleic acid using chain terminators, in which at least one of the chain terminators has as precursor a compound corresponding to the formula:

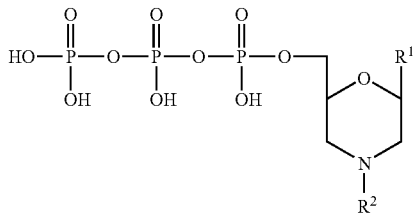
(I)

in which R¹ represents a nucleic base and R² represents a group corresponding to one of the following formulae:

—(CH₂)ₙ—NH₂  —(CH₂)ₙ—SH

—(CH₂)ₙ—COOH  —(CH₂)ₙ—OH

—(CH₂)ₙ—NH—R³  —(CH₂)ₙ—SR³

—(CH₂)ₙ—CO—R³  —(CH₂)ₙ—OR³ in which n is an integer ranging from 1 to 12 and R³ is a group derived from a label, a protein, an enzyme, a fatty acid or a peptide.

The chain terminators used in this process are nucleotide derivatives comprising a nucleic base R¹ which allows recognition by the polymerases and transcriptases, and compliance with the Watson and Crick rules of complementarity.

The nucleic bases used for R¹ may be natural or synthetic. The natural bases are generally chosen from adenine, guanine, cytosine, thymine, uracil, xanthine, hypoxanthine and 2-aminopurine, and derivatives thereof.

The synthetic bases are analogues or derivatives of the natural nucleic bases, which are capable of interacting with the natural bases.

Preferably, R¹ corresponds to one of the following formulae:

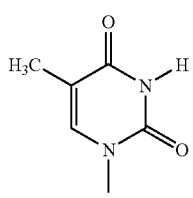 T

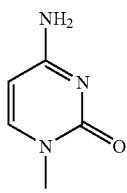 C

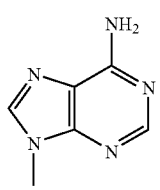 A

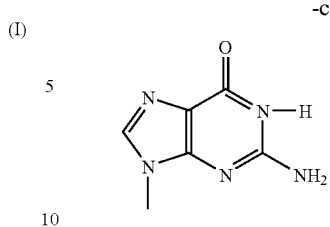 G

In the nucleotide derivatives of formula (I), the saccharide portion is replaced with a suitably substituted morpholine comprising:

1°) A hydroxymethyl function close to the ring oxygen, esterified with a triphosphoric acid group. This portion of the molecule mimics the 4',5' portion of nucleotides and allows binding by the polymerase or the transcriptase to the growing DNA or RNA chain.

2°) An amine function substituted with R2, which can optionally allow the grafting of a chromophore or of a biologically active group and, especially, which prevents the attachment of another nucleotide (interruption of the polymerization).

Compared with the derivatives conventionally used in the Sanger method, such as those described in documents [1], [2] and [3], these compounds may be synthesized in a single step directly from ribonucleoside triphosphates, as will be seen below.

The advantage of these compounds lies in the very wide choice of groups R² (substituents of the morpholine ring) which may be used and which allow this ring to be functionalized. Functions such as acids, amines, thiols or ethers may be added and will allow the grafting of varied chemical compounds, in particular of labels that are useful for indentifying DNA or RNA fragments.

The label used for R³ may be chosen from a very large set of molecules known for labelling nucleotides. They may be chosen, for example, from radioactive products, luminescent, electroluminescent and fluorescent products, molecules capable of coupling with other molecules, molecules allowing interactions of antigen-antibody type, and enzymatic labels.

Preferably, for the sequencing of nucleic acids, R³ is a fluorophore chosen, for example, from any fluoroscein or rhodamine derivative. Biotin derivatives may also be used. In particular, derivatives used for labelling nucleic acids will be chosen.

Nucleoside derivatives in which the saccharide portion of the nucleoside has been replaced with a morpholine have already been synthesized in the prior art, as is seen in the following documents:

Hileman et al., Bioconjugate Chemistry, 5, 1994, pages 436-444 [4],

Broker et al., Nucleic Acids Research, 5, 1978, pages 363-385 [5],

Agrawal et al., Nucleic Acids Research, 14, 1986, pages 6227-6245 [6],

FR-A-2 710 068 [7], and

Rayford et al., Journal of Biological Chemistry, 260, 1985, pages 15708-15713, [8].

The nucleoside derivatives in document [4] comprise a morpholino ring which is substituted with a fluorescein or a rhodamine. They are used for the study of proteins rather than as chain terminators in a nucleic acid sequencing process.

Their manufacture differs from that of the process reported herein, since the fluorophore is incorporated directly onto the morpholine ring. The technique we are describing involves a step of intermediate purification which allows us to isolate and fully characterize the final product, in contrast with Hileman et al.

Document [5] concerns transfer RNA modified at its 3' end with a nucleoside derivative comprising a morpholine ring substituted with a biotin. This product is used as a chemical label for transfer RNAs to study the chromosomal localization of transfer RNA genes.

Document [6] concerns an oligonucleotide comprising a morpholine ring coupled to a biotin, which is used as a probe for detecting and isolating specific genes.

Document [7] describes nucleoside derivatives comprising a substituted morpholine ring. They are used for preparing antibodies raised against a hapten bound to the morpholine ring of the nucleoside derivative.

Document [8] illustrates a morpholinoadenosine substituted with $CH_2COOH$, which is used for affinity chromatography.

Thus, none of these documents concerns the use of nucleotide derivatives such as those of the invention, as chain terminators, in a nucleic acid sequencing process according to the Sanger method.

The nucleotide derivatives used in the process of the invention may be prepared in a single step, directly from ribonucleoside triphosphates, according to the following reaction scheme illustrated with $R^1$ representing adenine.

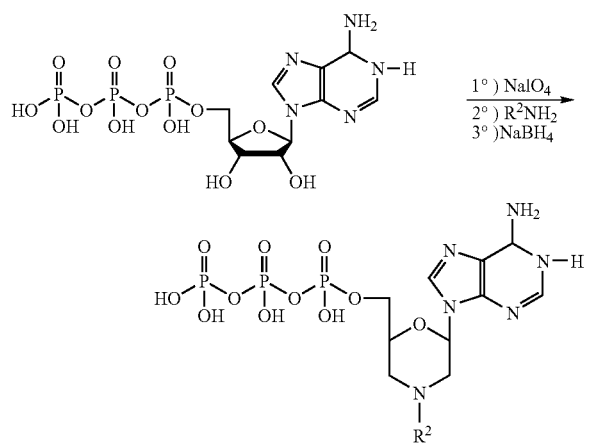

This process is of the same type as the processes described in documents [6] and [7] for forming the morpholino ring.

The nucleotide derivatives of formula (I) may also be prepared from morpholino-nucleosides and the triphosphate group may then be introduced using the Eckstein protocol, as described by Ludgwig et al. in J. Org. Chem. 54, 1989, pages 631-635 [9].

The enzymes which may be used for the enzymatic polymerization may be those described below.

According to the invention, the process for preparing morpholino-nucleotides of formula (I) comprises the reaction of a nucleoside triphosphate of formula:

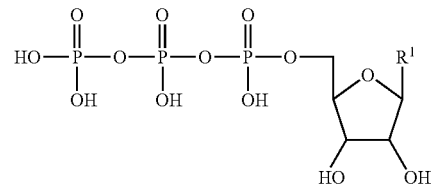

in which $R^1$ has the meaning given above, with a periodate, a compound of formula $R^2NH_2$ in which $R^2$ has the meaning given above, and sodium borohydride.

The invention also relates to the use of a nucleotide derivative having as precursor a compound of formula (I) for the labelling at the 3' end of nucleic acid (DNA or RNA) fragments by enzymatic incorporation of the nucleotide derivative at the 3' OH end of the nucleic acid fragment.

The invention also relates to the process for manufacturing a 3'-labelled nucleic acid (DNA or RNA) fragment by enzymatic incorporation of the nucleotide derivative mentioned above into the 3' OH end of the nucleic acid fragment.

The enzyme may be the Klenow fragment of the DNA polymerase, and in this case a template is then used to bind the morpholino-nucleoside to the nucleic acid fragment which serves as primer.

The enzyme used may also be a heat-resistant polymerase of a thermophilic bacterium or terminal transferase or reverse transcriptase.

The DNA or RNA fragments thus labelled can be used to block any subsequent ligation and to ensure protection against exonucleases, and also to detect DNA or RNA fragments.

A modified morpholino-nucleotide having as precursor a compound of formula (I) may also be used to modify a nucleic acid (DNA or RNA) fragment by enzymatic incorporation into the 3' end thereof of a modified morpholino-nucleotide having as precursor a compound of formula (I) comprising as $R^3$ a compound chosen from photo-crosslinking agents, for example for crosslinking to DNA or to any support; fatty acids, hydrophobic peptides or antibodies, for example to facilitate the penetration into cells, enzymes or portions of enzymes such as alkaline phosphatases, peroxidases or acetylcholinesterases for the detection, restriction enzymes for cleaving the vicinal DNA, and fluorophores.

As previously, the incorporation of this modified morpholino-nucleotide is carried out enzymatically. The nitrogenous bases, the labels and the enzymes which may be used may be the same as those mentioned above.

According to the invention, the nucleotide derivative, the modified morpholino-nucleotide and the chain terminator used, respectively, for the 3' labelling of nucleic acid fragments, for the modification of nucleic acid fragments or for the sequencing of a nucleic acid, may be the compound (I) in monophosphate form.

Other characteristics and advantages of the invention will emerge more clearly on reading the description which follows of preparation examples, which are obviously given for illustrative purposes and with no implied limitation, with reference to the attached drawing.

BRIEF DESCRIPTION OF THE FIGURES

FIG. 3 is a scheme illustrating the result on polyacrylamide gel of a test for monitoring the elongation of an oligonucleotide B and the incorporation of morpholino A putrescine.

FIG. 4 is a scheme illustrating the result on polyacrylamide gel of a test for monitoring the elongation of an oligonucleotide A and the incorporation of morpholino A putrescine or morpholino A fluorescein.

FIG. 5 illustrates hybridization of a primer strand with a DNA template strand followed by incorporation of 5' thymidine triphosphate into the primer strand by a DNA polymerase.

FIG. 6 illustrates hybridization of a primer strand with a DNA template strand followed by incorporation of 3'-deoxythymidine 5'-triphosphate into the primer strand by a DNA polymerase.

DETAILED DESCRIPTION OF THE EMBODIMENTS

Figure 1:
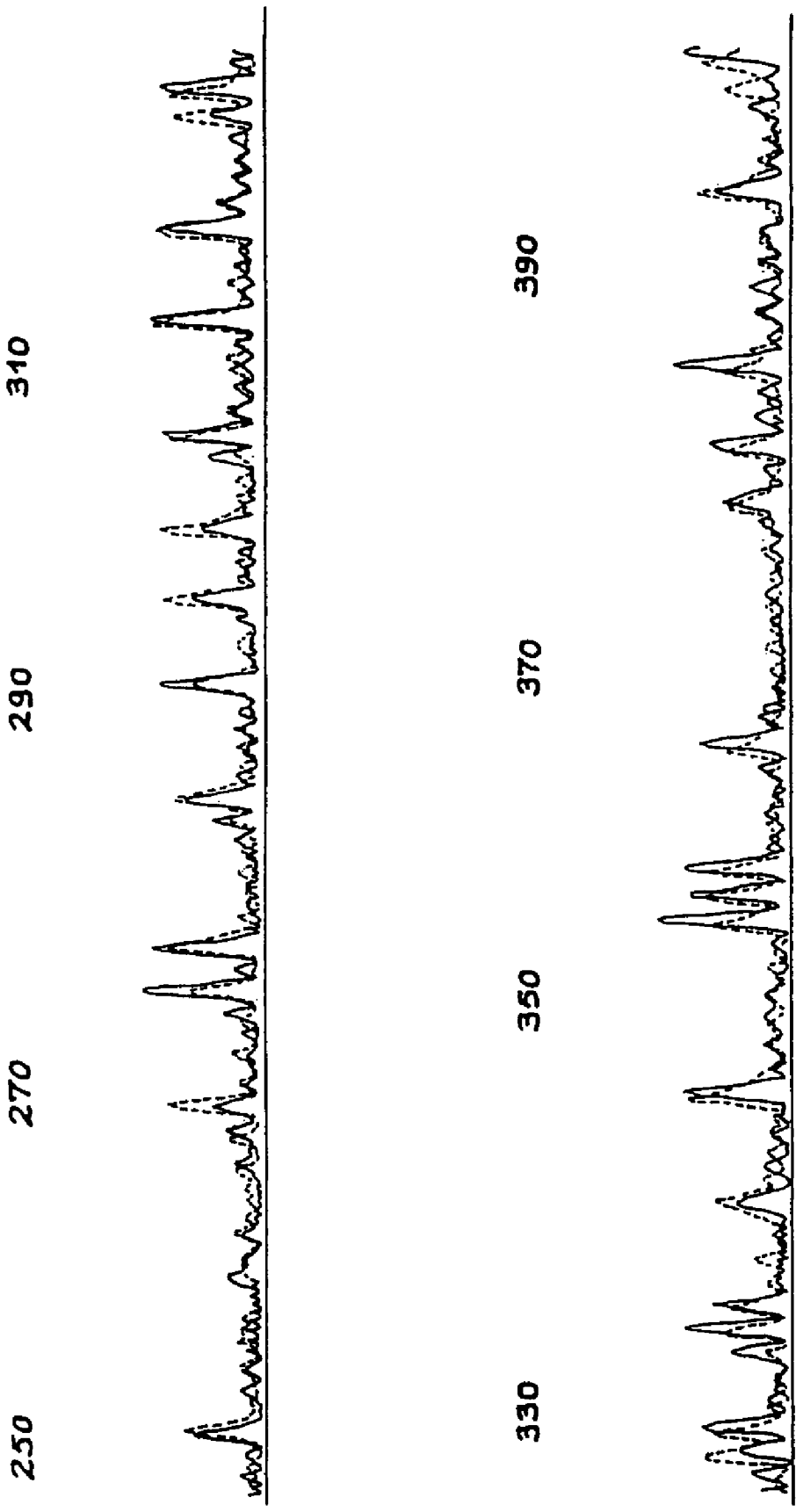
FIG. 1 is a diagram illustrating the results obtained for the sequencing of plasmid DNA with the chain terminator of the invention (solid-line curve) and with the chain terminator of the prior art (dashed-line curve).

Examples 1 to 4 which follow illustrate the synthesis of morpholino-nucleotides of formula (I).

Example 1

Synthesis of 4-(carboxymethyl)-2-(adenosin-9-yl)-6-(hydroxymethyl)morpholine 6-triphosphate (morpholino A glycine) 1

This morpholino A glycine 1 corresponds to formula (I) in which $R^1$ is adenine and $R^2$ is a —$CH_2$—COOH group.

In this example, all the reactions are carried out at room temperature, with magnetic stirring, in a 50 mL round-bottomed flask.

1.000 g, (1.8 mmol, 1 eq.) of 5'-adenosine triphosphate is dissolved in 10 mL of water and 1 eq. of sodium periodate (388 mg, 1.8 mmol) is then added. The solution is then stirred for 35 minutes.

Glycine (682 mg, 9.1 mmol, 5 eq.) dissolved in 2 mL of water (pH=9.5-10) is added and the pH of the solution is raised to 9.5-10 with solid potassium carbonate. The solution is stirred for 55 minutes. The reaction mixture turns yellow.

Sodium borohydride (166 mg in total, 4.4 mmol, 2.5 eq.) is added in six equivalent portions, each dissolved in 0.2 mL of water. After adding the first portion, an evolution of gas is noted. The other portions, each dissolved just before addition, are added every hour.

After leaving overnight, the solution is neutralized by adding 1M formic acid to pH 4-5, and is then evaporated.

An analysis by chromatography of reverse-phase polarity on a Merck LiChrocart 125-4 LiChrospher 100 RP-18 column ("endcapped", 5 μm, 125×4 mm) using a flow rate of 1 mL/min and 25 mM triethylammonium acetate TEAA/methanol MeOH [98/2] as eluent, indicates a yield of 40% (k'=3.85).

Purification:

this is performed by preparative high performance liquid chromatography (HPLC) using a Macherey Nagel Nucleosil 7 C-18 column (7 μm, 250×21 mm) with a flow rate of 8 mL/min and 25 mM triethylammonium bicarbonate TEAB as eluent.

Characterization:
$^1$H NMR: δ (ppm): 8.47 (s, 1H, H2), 8.37 (s, 1H, H8), 6.26 (dd, 1H, H1'), 4.54 (m, 1H, H4'), 4.28 (m, 1H, H5"), 4.22 (m, 1H, H5'), 3.70 (m, 1H, H2'), 3.68 (s, 2H, $CH_2$-glycine), 3.41 (m, 1H, H2"), 3.45 (m, 1H, H3'), 3.30 (m, 1H, H3"),
$^{13}$C NMR: δ (ppm): 152.7 (C2), 140.5 (C8), 78.6 (C1'), 74.1 (C4'), 66.4 (C5'), 60.6 ($CH_2$), 54.5 (C2'), 53.6 (C3')
$^{31}$P NMR: δ (ppm): −6.44 (d, 1P, γP), −11.68 (d, 1P, αP), −22.11 (t, 1P, βP)
Mass spectrometry: M−H$^-$=547.04 g.mol$^{-1}$

Example 2

Synthesis of 4-(carboxymethyl)-2-(thymidin-1-yl)-6-(hydroxymethyl)morpholine 6-triphosphate (morpholino T glycine) 4

This compound 4 corresponds to formula (I) with $R^1$ representing thymine and $R^2$ representing a —$CH_2$—COOH group.

In this example, the morpholino-nucleoside is first prepared and is then converted to a triphosphate.

a) Preparation of the Ribothymidine Morpholino-Nucleoside 2

All the reactions are carried out at ambient temperature, with magnetic stirring, in a 250 mL round-bottomed flask.

Ribothymidine (3.500 g, 13.5 mmol, 1 eq) is dissolved in 35 mL of water and 1 eq. of sodium periodate (2.900 g, 13.5 mmol) is then added. The solution is then stirred for 45 minutes.

Glycine (5.089 g, 67.8 mmol, 5 eq) in 35 mL of water (pH=9.5-10) is added and the pH of the solution is raised to 9.5-10 with potassium carbonate. The solution is stirred for 1 hour 45 minutes. The reaction mixture turns yellow.

One sixth of sodium borohydride (1.280 g in total, 33.8 mmol, 2.5 eq) dissolved in 3.5 mL of water is added to the solution. An evolution of gas is noted. The other sixths, each dissolved just before addition, are added every hour.

After leaving overnight, the solution is neutralized by adding 1M formic acid to pH 4-5, and is then evaporated.

An analysis by chromatograpgy of reverse-phase polarity on a Merck LiChrocart 125-4 LiChrospher 100 RP-18 column ("endcapped", 5 μm, 125×4 mm), with a flow rate of 1 mL/min, using as eluent: 25 mM TEAA/MeOH [99/1], indicates a yield of 32% (k'=8.83).

Purification:

this is performed by "flash" chromatography on a column of C-18 silica or reverse-phase polarity (Matrex, Amicon). The eluent is water.

Characterization:
$^1$H NMR: δ (ppm): 7.77 (s, 1H, H6), 5.92 (dd, 1H, H1'), 4.07 (m, 1H, H4'), 3.77 (m, 2H, H5', H5"), 3.22 (s, 2H, $CH_2$ glycine), 3.13 (dd, 1H, H2"), 2.99 (dd, 1H, H3"), 2.51 (t, 1H, H2'), 2.34 (t, 1H, H3'), 1.98 (s, 3H, $CH_3$ base).

b) Preparation of the Ribothymidine Morpholino-Nucleoside Monophosphate 3

234 μL of phosphorus oxychloride trichloride (2.5 mmol, 1.5 eq.) are added to 342 mg of imidazole (5.0 mmol, 3 eq) dried in a desiccator and then taken up in 5 mL of rigorously anhydrous pyridine. The mixture is stirred for 30 minutes under dry air.

In parallel, 500 mg of the morpholinothymidine (1.7 mmol, 1 eq.) obtained in a) are dried 3 times in pyridine and then taken up in 5 mL of anhydrous pyridine.

The imidazole/POCl$_3$/pyridine mixture under argon is added to the morpholinonucleoside solution and the whole is stirred for 48 hours at ambient temperature. Next, 100 µL of water are added, taking care to cool the reaction flask in an ice bath. The reaction mixture is evaporated to dryness and then taken up twice with water and evaporated in order to remove the pyridine.

An analysis by chromatography of reverse-phase polarity on a Macherey Nagel Nucleosil 5 C-18 column (7 µm, 120×3 mm), at a flow rate of 1 mL/min, using as eluent: 25 mM TEAA/MeOH [97/3], indicates a yield of 33% (k'=0.62).

Purification:
this is performed by preparative HPLC on H: Macherey Nagel Nucleosil 7 C-18 column (7 µm, 250×21 mm) at a flow rate of 5 mL/min using water as eluent.

Characterization:
$^1$H NMR: δ (ppm): 7.80 (s, 1H, H6), 5.95 (dd, 1H, H1'), 4.19 (m, 1H, H4'), 3.94 (t, 2H, H5', H5"), 3.28 (s, 2H, CH$_2$ glycine), 3.24 (m, 1H, H2"), 3.10 (m, 1H, H3"), 2.53 (t, 1H, H2'), 2.39 (t, 1H, H3'), 2.00 (s, 3H, CH$_3$ base)

$^{31}$P NMR δ (ppm): 1.74 (s)

c) Preparation of the Ribothymidine Morpholino-Nucleoside Triphosphate 4

1.097 g of carbonyldiimidazole (6.7 mmol, 5 eq.) dissolved in 5 mL of anhydrous dimethylformamide are added to the tributylammonium salt of the thymine morpholinonucleoside monophosphate 3 obtained in b) (511 mg, 1.3 mmol, 1 eq.) dissolved in 3 mL of anhydrous dimethylformamide. The mixture is stirred ate ambient temperature for five hours. The excess carbonyldiimidazole is destroyed by adding 436 µL of methanol (10.8 mmol, 8 eq.). After 30 minutes, 5 equivalents of tributylammonium pyrophosphate (3.008 g, 6.7 mmol) dissolved in 5 mL of dimethylformamide are added. The mixture is stirred for 2 days and the reaction mixture is then filtered and evaporated to dryness.

An analysis by chromography of reverse-phase polarity is carried out on an SFCC PVDI 31 column (5 µm, 100×4.6 mm), at a flow rate of 1 mL/min, using as eluent a gradient of ammonium formate (AF), under the following conditions:

| t (min) | 25 mM AF (%) | 0.9 M AF (%) |
|---|---|---|
| 0 | 100 | 0 |
| 10 | 100 | 0 |
| 40 | 0 | 100 |
| 41 | 0 | 100 |
| 43 | 100 | 0 |

This indicates a yield of 27% (k'=13.84).

Purification:
this is performed by "flash" chromatography on a column of ion-exchange phase (DEAE Sepharose Fast Flow, Pharmacia Biotech). The eluent is a gradient of TEAB (from 25 mM to 0.9 M).

Characterization:
$^1$H NMR: δ (ppm): 7.74 (s, 1H, H6), 5.92 (dd, 1H, H1'), 4.25 (m, 1H, H4'), 4.15 (m, 2H, H5', H5"), 3.81 (s, 2H, CH$_2$ glycine), 3.54 (d, 1H, H2"), 3.10 (t, 1H, H3"), 2.56 (t, 1H, H2'), 2.45 (t, 1H, H3'), 1.95 (s, 3H, CH$_3$ base)

$^{31}$P NMR: δ (ppm): −10.03 (d, 1P, γP), −10.88 (d, 1P, αP), −22.65 (t, 1P, βP)

Mass spectrometry: M−H$^-$=540,41 g.mol$^{-1}$

Example 3

Synthesis of 4-(carboxymethyl-2-(guanin-9-yl)-6-(hydroxymethyl)morpholine 6-triphosphate (morpholino G glycine) 5

This morpholino G glycine 5 corresponds to formula (I) with R$^1$=guanine and R$^2$=—CH$_2$COOH.

Guanosine 5'-triphosphate (50 mg, 0.08 mmol, 1 eq.) is dissolved in 2 mL of water and 1 eq. of sodium periodate (18 mg, 0.08 mmol) is then added. The solution is then stirred for 35 minutes. Glycine (31 mg, 0.42 mmol, 5 eq.) dissolved in 2 mL (pH=9.5-10) [lacuna] is added and the pH of the solution is raised to 9.5-10 with solid potassium carbonate (monitored with pH paper). The solution is stirred for 45 minutes. Sodium borohydride (8 mg in total, 0.21 mmol, 2.5 eq.) is added in six equivalent portions, each dissolved in 0.1 mL of water. The other fractions, each dissolved just before addition, are added every hour. After leaving overnight, the solution is neutralized by adding 1M formic acid to pH 4-5 and is then evaporated.

An analysis by chromatography of reverse-phase polarity (System E) in an SFCC PVDI 31 column (5 µm, 100×4.6 mm), with a flow rate: 1 mL/min, using as eluent a gradient of ammonium formate, under the following conditions:

| t (min) | 25 mM AF (%) | 1 M AF (%) |
|---|---|---|
| 0 | 100 | 0 |
| 3 | 100 | 0 |
| 10 | 0 | 100 |
| 15 | 0 | 100 |
| 17 | 100 | 0 |

This analysis give a yield of 39% (k'=5.5).

Compound 5 is purified by preparative HPLC using System F: Vydac Sax-Protein column (8 µm, 100×4.6 mm). Flow rate: 10 mL/min. Eluent: gradient of ammonium formate, under the following conditions:

| t (min) | 25 mM AF (%) | 1 M AF (%) |
|---|---|---|
| 0 | 100 | 0 |
| 3 | 100 | 0 |
| 10 | 0 | 100 |
| 15 | 0 | 100 |
| 17 | 100 | 0 |

14 mg of compound 5 are obtained, i.e. a yield of 26.1%.

Characterization:
$^1$H NMR (Brüker AM 400): δ (ppm): 8.07 (s, 1H, H8); 6.06 (dd, 1H1, H1') 4.51 (m, 1H, H4'); 4.22 (m, 2H, H5', H5"); 3.71 (m, 1H, H2"); 3.67 (s, 2H, —CH$_2$ glycine); 3.46 (m, 1H, H3"); 3.38 (m, 1H, H2'); 2.95 (m, 1H, H3').

$^{13}$C NMR (Brüker AM 400): δ (ppm): 173.50 (—COOH); 158.91 (C6); 153.98 (C2); 151.07 (C4); 137.39 (C8); 115.94 (C5); 77.87 (C 1'); 73.62 (C4'); 65, 61 (C5'); 59.98 (—CH$_2$—); 53.28 (C2'); 51.88 (C3').

$^{31}$P NMR (U 400 Varian) δ (ppm): −7.14 (d, 1P, γP); 8.68 (d, 1P, αP); −20.28 (t, 1P, βP).

Mass spectrometry (LCQ machine in positive mode):

i. $M+H^+=564.9$ g.mol$^{-1}$.

UV spectrum: λmax=256 nm.
Capillary electrophoresis:

i. $\mu ep=-4.28\times 10^{-4}$ cm$^2$.V$^{-1}$.s$^{-1}$.

Example 4

Synthesis of 4-(carboxymethyl)-2-(cytosin-1-yl)-6-(hydroxymethyl)morpholine 6-triphosphate (morpholino C glycine) 6

Compound 6 corresponds to formula (I) with $R^1$=cytosine and $R^2$=—CH$_2$—COOH.

All the reactions are carried out at ambient temperature, with magnetic stirring, in a 20 mL round-bottomed flask.

The reaction is the same as for compound 5, starting with cytosine 5'-triphosphate (50.0 mg, 0.09 mmol, 1 eq.), sodium periodate (21 mg, 0.09 mmol, 1 eq.), glycine (36 mg, 0.48 mmol, 5 eq.) dissolved in 2 mL of water (pH=9.5-10) and sodium borohydride (9 mg in total, 0.23 mmol, 2.5 eq.), added in six equivalent portions, each dissolved in 0.05 mL of water.

An analysis by chromatography on an ion-exchange phase column (System E), as in Example 3, indicates a capacity factor k'=4.08.

The product is purified by semi-preparative HPLC using System F as in Example 3.

17 mg of product are isolated, which corresponds to a yield of 24.3%.

Characterization:
$^1$H NMR (Brüker AM 400): δ (ppm): 7.93 (d, 1H, H6); 6.25 (dd, 1H, H1'); 6.20 (d, 1H, H5); 4.51 (m, 1H, H4'); 4.27 (m, 2H, H5', H5"); 3.85 (m, 4H, H2"+H3"+—CH$_2$ glycine); 3.33 (t, 1H, H2'); 3.22 (t, 1H, H3').

$^{13}$C NMR (Brüker AM 400): δ (ppm): 173.05 (—COOH); 165.13 (C4); 154.23 (C2); 140.93 (C6); 95.48 (C5); 80.42 (C1'); 78.44 (C4'); 69.37 (C5'); 64.57 (—CH$_2$—); 54.66 (C2'); 53.67 (C3').

$^{31}$P NMR (Brüker WM 250): δ (ppm): −7.99 (d, 1P, γP); −10, −10 (d, 1P, αP); −21.28 (t, 1P, βP).

Mass spectrometry
(VG ZAB-2-EQ machine, negative mode):

M−H$^-$=521.9 g.mol$^{-1}$.

UV spectrum: λmax=270 nm
Capillary electrophoresis:

$\mu ep=-4.28\times 10^{-4}$ cm$^2$.V$^{-1}$.s$^{-1}$.

Example 5

Synthesis of 4-(aminobutyl)-2-(adenosin-9-yl)-6-(hydroxymethyl)morpholine 6-triphosphate (morpholino A putrescine) 7

This morpholino A putrescine 7 corresponds to formula (I) with $R^1$ representing adenine and $R^2$ representing a —(CH$_2$)$_4$—NH$_2$ group.

All the reactions are carried out at ambient temperature, with magnetic stirring, in a 100 mL flask. Adenosine 5'-triphosphate (500 mg, 0.9 mmol, 1 eq.) is dissolved in 10 mL of water and 1 eq. of sodium periodate (194 mg, 0.9 mmol) is then added. The solution is then stirred for 45 minutes.

Putrescine (456 μL, 4.5 mmol, 5 eq.) is added. The solution is stirred for 45 minutes. The reaction mixture turns yellow.

One sixth of sodium borohydride (86 mg in total, 2.3 mmol, 2.5 eq.) dissolved in 0.1 mL of water is added to the solution. An evolution of gas is noted. The other sixths, each dissolved just before addition, are added every hour.

After leaving overnight, the solution is neutralized by adding 1M formic acid to pH 4-5 and is then evaporated.

An analysis by chromatography of reverse-phase polarity is carried out on a Merck LiChrocart 125-4 LiChrospher 100 RP-18 column ("endcapped", 5 μm, 125×4 mm) with a flow rate of 1 ml/min, using as eluent a 25 mM TEAB/MeOH gradient, under the following conditions:

| t (min) | TEAB (%) | MeOH (%) |
| --- | --- | --- |
| 0 | 97 | 3 |
| 2 | 97 | 3 |
| 10 | 90 | 10 |
| 15 | 90 | 10 |
| 17 | 97 | 3 |

This analysis indicates a yield of 67% (k'=3.81).

Product 7 is purified by semi-preparative HPLC on a Phenomenex Ultremex 5-C18 column (250×10 mm) with a flow rate of 4 mL/min, and using as eluent a 25 mM TEAB/MeOH gradient, under the following conditions:

| t (min) | TEAB (%) | MeOH (%) |
| --- | --- | --- |
| 0 | 95 | 5 |
| 3 | 95 | 5 |
| 8 | 90 | 10 |
| 10 | 95 | 5 |

Characterization:
$^1$H NMR: δ (ppm): 8.44 (s, 1H, H2), 8.33 (s, 1H, H8), 6.06 (dd, 1H, H1'), 4.35 (m, 1H, H4'), 4.22 (m, 2H, H5', H5"), 3.39 (d, 1H, H2'), 3.22 (t, 1H, H3"), 3.14 (s, 2H, CH$_2$ putrescine), 2.92 (t, 1H, H2'), 2.74 (s, 2H, CH$_2$ putrescine), 2.54 (t, 1H, H3'), 1.78 (s, 4H, (CH$_2$)$_2$ putrescine).

$^{31}$P NMR: δ (ppm): −8.45 (dd, 1P, γP), −13.25 (dd, 1P, αP), −24.20 (t, 1P, βP)

Mass spectrometry: $M+H^+$=561.92 g.mol$^{-1}$

Example 6

Synthesis of 4-(aminobutyl)-2-(thymidin-1-yl)-6-(hydroxymethyl)morpholine 6-triphosphate (morpholino T putrescine) 9

Compound 9 corresponds to formula (I) with $R^1$=thymine and $R^2$=—(CH$_2$)$_4$—NH$_2$.

Preparation of 4-(aminobutyl)-2-(thymidin-1-yl)-6-(hydroxymethyl)morpholine-6-hydroxyl 8

All the reactions are carried out at ambient temperature, with magnetic stirring, in a 250 mL round-bottomed flask.

Ribothymidine (2.000 g, 7.74 mmol, 1 eq.) is dissolved in 30 mL of water and 1 eq. of (1.656 g, 7.75 mmol) of sodium periodate is then added. The solution is then stirred for 70 minutes. Putrescine (3.9 mL, 38.75 mmol, 5 eq.) is added. The solution is stirred for 50 minutes. The reaction mixture turns yellow.

One sixth of sodium borohydride (735 mg in total, 19.42 mmol, 2.5 eq.) dissolved in 0.25 mL of water is added to the solution. An evolution of gas is noted. The other sixths, each dissolved just before addition to 0.25 mL of water, are added every hour.

After leaving overnight, the solution is neutralized by adding 1M formic acid to pH 4-5 and is then evaporated. An analysis by chromatography of reverse-phase polarity is carried out using System G: Merck LiChrocart 125-4 LiChrospher 100 RP-18 column ("endcapped", 5 µm, 125×4 mm). Flow rate: 1 mL/min. Eluent: 25 Mm TEAB/CH$_3$CN gradient, under the following conditions:

| t (min) | 25 mM TEAB (%) | CH$_3$CN (%) |
|---|---|---|
| 0 | 100 | 0 |
| 4 | 100 | 0 |
| 15 | 85 | 15 |
| 18 | 100 | 0 |

This indicates a 76% yield (k'=5.7).

The product is purified by preparative HPLC using System H: Macherey Nagel Nucleosil 7 C-18 column (7 µm, 250×21 mm). Flow rate: 10 mL/min. Eluent: 25 mM TEAB/CH$_3$CN [85/15].

1.56 g of compound 8 are obtained, i.e. a 64.6% yield.

Characterization:

$^1$H NMR 1H (Brüker AC 200): δ (ppm): 7.69 (s, 1H, H6); 5.88 (dd, 1H, H1'); 4.01 (m, 1H, H4'); 3.80 (m, 1H, H5', H5"); 3.08 (m, 4H, H2", H3", 2Ha); 2.63 (m, 2H, 2 Hd); 2.33 (t, 1H, H2'); 2.22 (t, 1H, H3'); 1.98 (m, 3H, —CH3); 1.74 (m, 4H, 2 Hb, 2 Hc).

$^{13}$C NMR (Brüker AC 200): δ (ppm): 171.16 (C2); 154.58 (C4); 135.93 (C6); 110.46 (C5); 78.62 (C1'); 75.04 (C4'); 61.10 (C5'); 55.82 (C3'); 53.49 (C2'); 51.30 (Ca); 38.39 (Cd); 24.50 (Cc); 21.31 (Cb); 11.10 (—CH$_3$).

UV spectrum: λmax=266 nm.

b) Preparation of 4-(aminobutyl)-2-(thymidin-1-yl)-6-(hydroxymethyl)morpholine 6-triphosphate 9

Morpholinothymidine/putrescine 8 (249 mg, 0.80 mol, 1 eq.) is dried using a vane pump for 1 hour. 256 mg of Proton-sponge® (1.19 mmol, 1.5 eq.) are then added and 2 mL of anhydrous trimethyl phosphate are added; The medium is placed in an ice bath, with stirring, and 109 µL of phosphorus oxychloride are then added (2.24 mmol in total, 2.8 eq.). After 2 h 30 min, a further 50 mL of phosphorus oxychloride are added, and this operation is repeated 12 h later. Next, 8 mL of a 0.5M solution of pyrophosphate in the form of the tributylammonium salt (4.0 mmol, 5 eq.), in anhydrous DMF are added. The mixture is stirred at 0° C. for one minute and the medium is then dried on a rotavapor and vane pump.

An analysis by chromatography of reverse-phase polarity using System I: Vydac Sax-Protein column (8 µm, 100×4.6 mm) with a flow rate: 10 mL/min, using as eluent a gradient of ammonium formate, under the following conditions:

| t (min) | 25 mM AF (%) | 1M AF (%) |
|---|---|---|
| 0 | 100 | 0 |
| 1 | 100 | 0 |
| 15 | 70 | 30 |
| 17 | 100 | 0 |

This indicates a capacity factor k'=3.2.

The product is purified by preparative HPLC using System I described above.

48 mg of 9 are obtained, i.e. a 13.2% yield.

Characterization:

$^1$H NMR (Brüker AM 400): δ (ppm): 7.83 (s, 1H, H6); 6.31 (dd, 1H, H1'); 4.68 (m, 1H, H4') ; 4.39 (m, 1H, H5', H5"); 4.01 (d, 1H, H2"); 3.93 (d, 1H, H3"); 3.58 (m, 2H, 2 Ha); 3.51 (t, 1H, H2'); 3.41 (m, 1H, H3'); 3.28 (m, 2H, 2 Hd) ; 2.10 (s, 5H, —CH$_3$+2 Hb); 2.00 (m, 2H, 2Hc).

$^{13}$C NMR (Brüker AM 400): δ (ppm): 166.36 (C2); 151.03 (C4); 136.73 (C6); 112.42 (C5); 77.33 (C1'); 72.46 (C4'); 65.10 (C5'); 57.04 (C3); 51.71 (C2'); 51.13 (Ca); 98.91 (Cd); 23.85 (Cc); 20.50 (Cb); 11.62 (—CH$_3$).

$^{31}$P NMR (U 400 Varian): δ (ppm): −8.19 (s, 2P, γP, αP); −18.99 (t, 1p, βP).

Mass spectrometry (LCQ machine in negative mode): M-H$^-$=551.3 g.mol$^{-1}$.

UV spectrum: λmax=262 nm.

Capillary electrophoresis:

$\mu ep = -4.69 \times 10^{-4}$ cm$^2$.V$^{-1}$.s$^{-1}$.

EXAMPLE 7

Synthesis of 4-(aminobutyl)-2-(guanosin-9-yl)-6-(hydroxymethylmorpholine 6-triphosphate (morpholino G putrescine) 10

Compound 10 corresponds to formula (I) with R$^1$=guanine and R$^2$=—(CH$_2$)$_4$—NH$_2$.

All the reactions are carried out at ambient temperature, with magnetic stirring, in a 50 mL round-bottomed flask.

Guanosine 5'-triphosphate (50 mg, 0.17 mmol, 1 eq.) is dissolved in 5 mL of water and 1 eq. of sodium periodate (37 mg, 0.17 mmol, 1 eq.) is then added. The solution is then stirred for 30 minutes.

Putrescine (85 µL, 0.84 mmol, 5 eq.) is added and the pH of the solution is measured, and is equal to 10. If a lower value had been found, potassium carbonate would have been added to obtain this value. The solution is stirred for 45 minutes.

Sodium borohydride (8.7 mg in total, 0.45 mmol, 2.5 eq.) is added in six equivalent portions, each dissolved in 0.1 mL of water. The other fractions, each dissolved just before addition, are added every hour.

After leaving overnight, the solution is neutralized by adding 1M formic acid to pH 4-5 and is then evaporated.

Compound 10 is purified by precipitation from methanol followed by passage through 5 mL of Dowex resin in Na$^+$ form.

68 mg of compound 10 are obtained, i.e. a yield of 62.2%.

Characterization:

$^1$H NMR (Brüker AM 400): δ (ppm): 8.29 (s, 1H, H8); 6.31 (dd, 1H, H1'); 4.74 (m, 1H, H4'); 4.37 (m, 2H, H5', H5"); 3.99 (m, 1H, H2"); 3.96 (m, 1H, H3"); 3.79 (t, 1H, H2'); 3.47 (m, 2H, 2 Hb); 3.39 (t, 1H, H3'); 3.19 (m, 2H, 2 Hc); 2.06 (m, 2H, 2 Ha); 1.91 (m, 2H, 2 Hd).

$^{13}$C NMR (Brüker AM 400): δ (ppm): 151.11 (C6); 154.11 (C2); 149.91 (C4); 136.95 (C8); 113.46 (C5); 76.99 (C1'); 72.58 (C4'); 65.25 (C5'); 56.95 (Ca); 51.81 (C2'); 50.52 (C3'); 30.04 (Cd); 23.76 (Cc); 20.36 (Cb).

$^{31}$P NMR (U 400 Varian): δ (ppm): −8.28 (d, 1P, γP); −8.97 (d, 1P, αP); −20.45 (t, 1P, βP).

Mass spectrometry (LCQ machine in negative mode): M−H⁻=576.9 g.mol⁻¹.

UV spectrum: λmax=252 nm.

Capillary electrophoresis:

$\mu ep = -3.41 \times 10^{-4}$ cm$^2$.V$^{-1}$.s$^{-1}$.

EXAMPLE 8

Synthesis of 4-(aminobutyl)-2-(cytosin-1-yl)-6-(hydroxymethylmorpholine 6-triphosphate (morpholino C putrescine) 11

The entire reaction is carried out at ambient temperature, with magnetic stirring, in a 50 mL round-bottomed flask.

The reaction is the same as for compound 7, starting with cytosine 5'-triphosphate (50 mg, 0.09 mmol, 1 eq.), sodium periodate (20 mg, 0.09 mmol, 1 eq.), putrescine (47 μL, 0.47 mmol, 5 eq.) and sodium borohydride (9.1 mg in total, 0.24 mmol, 2.5 eq.) added in six equivalent portions, each dissolved in 0.1 mL of water.

An analysis by chromatography of reverse-phase polarity (System O): Merck Lichrocart 125-4 LiChrospher 100RP-18 column ("endcapped", 5 μm, 125×4 mm). Flow rate: 1 mL/min. Eluent: 25 mM TEAB/MeOH gradient, under the following conditions:

| t (min) | 25 mM TEAB (%) | MeOH (%) |
|---|---|---|
| 0 | 97 | 3 |
| 2 | 97 | 3 |
| 10 | 90 | 10 |
| 15 | 90 | 10 |
| 17 | 97 | 3 | indicates a capacity factor k'=4.18.

Compound 11 is purified by precipitation from methanol and then passage through 5 mL of Dowex resin in Na⁺ form.

47 mg of 11 are obtained, which corresponds to to a yield of 85.4%.

Characterization:

$^1$H NMR (Brüker AM 400): δ (ppm): 7.78 (d, 1H, H6); 6.17 (d, 1H, H5); 5.96 (dd, 1H, H1'); 4.22 (m, 1H, H4'); 3.91 (m, 2H, H5', H5"); 3.28 (m, 1H, H2"); 3.20 (m, 1H, H3"); 3.16 (m, 2H, 2 Ha); 2.80 (m, 2H, 2 Hd); 2.44 (m, 1H, H2'); 2.32 (m, 1H, H3'); 1.79 (m, 4H, 2 Hb+2 Hc).

$^{13}$C NMR (Brüker AM 400): δ (ppm): 166.056 (C4); 157.28 (C2); 142.43 (C6); 96.88 (C5); 80.57 (C1'); 75, 13 (C4'); 66.48 (C5'); 57.11 (Ca); 55.30 (C2'); 52.45 (C3'); 30.66 (Cd); 25.29 (Cc); 22.70 (Cb).

$^{31}$P NMR (Brüker WM 250): δ (ppm): −5.42 (d, 1P, γP); −10.06 (d, 1P, αP); −20.82 (m, 1P, βP).

Mass spectrometry (LCQ machine in negative mode): M−H⁻=536.0 g.mol⁻¹.

UV spectrum: λmax=268 nm

Capillary electrophoresis:

$\mu ep = -2.99 \times 10^{-4}$ cm$^2$.V$^{-1}$.s$^{-1}$.

EXAMPLE 9

Synthesis of 4-[5((2-aminobutyl)-thioureidyl)fluorescein)]-2-(adenosin-9-yl)-6-(hydroxy-methyl)morpholine 6-triphosphate (morpholino A putrescine-fluorescein) 12

This compound 12 corresponds to formula (I) with R$^1$ representing adenine and R$^2$ representing (CH$_2$)$_4$NHR$^3$ in which R$^3$ is a group derived from fluorescein.

All the reactions are carried out at ambient temperature, with magnetic stirring, in a 100 mL round-bottomed flask.

184.9 mg (0.5 mmol, 1.5 eq.) of fluorescein isothiocyanate are added gradually in three portions to 200 mg (0.3 mmol, 1 eq.) of morpholino A putrescine 7 of Example 5, in a water/pyridine mixture (1/1). The medium is stirred for 48 hours and then evaporated to dryness.

An analysis by chromatography of reverse-phase polarity on a Merck LiChrocart 125-4 LiChrospher 100 RP-18 column ("endcapped", 5 μm, 125×4 mm), with a flow rate of 1 mL/min using as eluent: 25 mM TEAA/MeOH [97/3], indicates a yield of about 48% (k'=7.51).

Purification:

this is performed by "flash" chromatography on a column of C-18 silica of reverse-phase polarity (Econosil prep 90, Alltech, France). The eluent is a water/MeOH gradient.

Characterization:

$^1$H NMR: δ (ppm): 8.57 (s, 1H, H2), 8.31 (s, 1H, H8), 8.20-6.65 (9H, fluorescein), 5.79 (dd, 1H, H1'), 4.25 (m, 1H, H4'), 4.11 (m, 2H, H5', H5"), 3.60 (s, 2H, CH$_2$ putrescine), 3.12 (d, 1H, H3"), 2.93 (d, 1H, H2"), 2.81 (m, 1H, H2'), 2.59 (m, 2H, CH$_2$ putrescine), 2.50 (dd, 1H, H3'), 1.79 (s, 2H, CH$_2$ putrescine), 1.62 (m, 2H, CH$_2$ putrescine)

$^{31}$P NMR: δ (ppm): −8.45 (dd, 1P, γP), −13.25 (dd, 1P, αP), −24.20 (t, 1P, βP)

Mass spectrometry: M−H⁻=949.2 g.mol⁻¹

EXAMPLE 10

Synthesis of 4-[5(((2-aminobutyl)-thioureidyl)fluorescein)-1-2-(thymidin-1-yl)-6-(hydroxy-methyl) morpholine 6-triphosphate (morpholino T putrescine fluorescein) 13

All the reactions are carried out at ambient temperature, with magnetic stirring, in a 25 mL round-bottomed flask.

31 mg (0.08 mmol, 1.5 eq.) of fluorescein isothiocyanate are added in three portions to 30 mg (0.05 mmol, 1 eq.) of compound 9 dissolved in 2 mL of a water/pyridine mixture (1/1). The medium is stirred for 48 hours and then evaporated to dryness.

Compound 13 is purified by semi-preparative high performance liquid chromatography, on a column of reverse-phase polarity (System L): Macherey Nagel Nucleosil 7 C-18 column (7 μm, 250×21 mm). Flow rate: 10 mL/min. Eluent: 25 mM TEAB/CH$_3$CN, under the following conditions:

| t (min) | 25 mM TEAB (%) | CH$_3$CN (%) |
|---|---|---|
| 0 | 100 | 0 |
| 4 | 100 | 0 |
| 15 | 73 | 27 |
| 18 | 100 | 0 |

Characterization:

Mass spectrometry (LCQ machine in positive mode):

$M-H^+=942.1$ g.mol$^{-1}$.

UV spectrum: λmax=488 nm.
Capillary electrophoresis:

$\mu cp=-4.23\times10^{-4}$ cm$^2$.V$^{-1}$.s$^{-1}$.

EXAMPLE 11

Synthesis of 4-[5(((2-aminobutyl)-thioureidyl)fluorescein)]-2-(guanosin-9-yl)-6-(hydroxy-methyl)morpholine 6-triphosphate (morpholino G putrescine fluoresceine) 14

All the reactions are carried out at ambient temperature, with magnetic stirring, in a 25 mL round-bottomed flask.

30 mg (0.08 mmol, 1.5 eq.) of fluorescein isothiocyanate are added gradually in three portions to 30 mg (0.05 mmol, 1 eq.) of compound 10 dissolved in 2 mL of a water/pyridine mixture (1/1). The medium is stirred for 48 hours and then evaporated to dryness.

An analysis by chromatography of reverse-phase polarity (System M): Merck-LiChrochart 125-4 LiChrospher 100 RP-18 column ("endcapped",5 μm, 125×4 mm). Flow rate: 1 mL/min. Eluent: 25 mM TEAB/CH$_3$CN gradient, under the following conditions:

| t (min) | 25 mM TEAB (%) | CH$_3$CN (%) |
|---|---|---|
| 0 | 100 | 0 |
| 4 | 100 | 0 |
| 15 | 73 | 27 |
| 18 | 100 | 0 | indicates a yield of about 24% (k'=4.62).

Compound 14 is purified by semi-preparative high performance liquid chromatography, on a column of reverse polarity, using System L of Example 10.

14.5 mg of compound 14 are obtained, i.e. a yield of 30.0%.

Characterization:

$^1$H NMR (Brüker AM 400): δ (ppm): 7.87 (s, 1H, H8); 7.70-6.63 (9H, fluorescein); 5.60 (dd, 1H, H1'); 4.18 (m, 1H, H4'); 4.12 (m, 2H, H5', H5''); 3.82 (m, 1H, Ha); 3.61 (m, 1H, Ha); 3.08 (d, 1H, H3''); 2.95 (d, 1H, H2''); 2.82 (m, 1H, H2'); 2.71 (m, 1H, Hd); 2.55 (m, 1H, Hd); 2.39 (t, 1H, H3'); 1.77 (m, 2H, 2 Hb); 1.62 (m, 2H, 2 Hc).

$^{13}$C NMR (Brüker AM 400): δ (ppm): 180.58 (several fluorescein C); 158.37 (several fluorescein C); 136.98 (C6); 131.06 (C2); 126.7 (C4); 122.85 (several fluorescein C); 112.03 (C8); 103.80 (several fluorescein C); 78.91 (C1'); 74.83 (C4') 65.96 (C5'); 57.27 (Ca); 53.79 (C2'); 52.56 (C3'); 48.87 (Cd); 25.70 (Cc); 22.75 (Cb).

$^{31}$P NMR (U 400 Varian): δ (ppm): −4.93 (dd, 1P, γP); −9.82 (d, 1P, αP); −19.94 (t, 1P,βP).

Mass spectrometry (LCQ machine in negative mode): $M-H^-=985.3$ g.mol$^{-1}$.

UV spectrum: λmax=494 nm
Capillary electrophoresis:

$\mu ep=-3.83>10^{-4}$ cm$^2$.V$^{-1}$.s$^{-1}$.

EXAMPLE 12

Synthesis of 4-[5(((2-aminobutyl)-thioureidyl)fluorescein)]-2-(cytosin-1-yl)-6-(hydroxy-methyl)morpholino 6-triphosphate (morpholino C putrescine-fluorescein) 15

All the reactions are carried out at ambient temperature, with magnetic stirring, in a 10 mL round-bottomed flask.

36 mg (0.09 mmol, 1.5 eq.) of fluorescein isothiocyanate are added in three portions to 30 mg (0.05 mmol, 1 eq.) of compound 11, dissolved in 2 mL of a water/pyridine mixture (1/1). The medium is stirred for 48 hours and then evaporated to dryness.

An analysis by chromatography of reverse-phase polarity (System M described in Example 11) indicates a capacity factor k'=4.7.

Compound 15 is purified by semi-preparative high performance liquid chromatography, on a column of reverse-phase polarity (System L of Example 10).

22.7 mg of compound 15 are obtained, i.e. a yield of 44.3%.

Characterization:

$^1$H NMR (Brüker AM 400): δ (ppm): 7.99 (s, 1H, H6); 7.87-6.69 (9H, fluorescein); 5.78 (d, 2H, H5+H1'); 4.14 (m, 1H, H4'); 3.77 (m, 2H, H5', H5''); 3.36 (m, 2H, 2 Ha); 3.32 (m, 1H; H2''); 3.03 (m, 1H, H3''); 2.81 (m, 1H, H2'); 2.69 (m, 2H, 2 Hd, 1.79); 2.30 (m, 1H, H3'); 1.79 (m, 2H, 2 Hb); 1.68 (m, 2H, 2 Hc)

$^{13}$C NMR (Brüker AM 400): δ (ppm): 175.06 (several fluorescein C); 157.62 (C2); 141.39 (several fluorescein C); 131.56 (C6); 121.06 (several fluorescein C); 114.60 (several fluorescein C); 103.30 (several fluorescein C); 96.53 (C5); 79.10 (C1'); 73.67 (C4'); 65.42 (C5'); 58.89 (Ca); 57.19 (C2'); 51.78 (C3'); 46.61 (Cd); 25.48 (Cc); 21.38 (Cb)

$^{31}$P NMR (U 400 Varian): δ (ppm) −2.97 (d, 1P, γP); −7.54 (d, 1P, αP); −18.56 (m, 1P, βP).

Mass spectrometry (LCQ machine in negative mode): $M-H^-=925.2$ g.mol$^{-1}$.

UV spectrum: λmax=491 nm.
Capillary electrophoresis:

$\mu ep=-4.26\times10$ cm$^2$.V$^{-1}$.s$^{-1}$.

EXAMPLE 13

Use of Morpholino T Glycine for the Analysis of a DNA Sequence

The morpholino T glycine 4 of Example 2 is tested in sequence reaction with fluorescent primers (Applied Biosystems, Perkin-Elmer, Foster City, Calif., USA) on a standard template which is a Bluescript plasmid DNA (Stratagene, La Jolla, Calif., USA). The enzyme used is a Taq polymerase (Perkin-Elmer), which is used in its buffer (TACS buffer, Perkin-Elmer).

Two reactions are carried out with morpholino T glycine at 200 and 500 μM (Table 4), and also two control reactions (Table 5) with dideoxynucleotide T (Boehringer).

The reaction medium, of a total volume of 10 μL, contains 125 ng of template, 1.25 pmol of fluorescent primer and the other constituents given in Tables 4 and 5. The medium is subjected to heat cycles in order to produce in number molecules of newly formed DNA strands. An amplification on an Perkin-Elmer 9700 machine is performed, according to the following sequences: 3 min., 95° C.; 15 cycles (15 sec., 95° C.; 15 sec., 55° C.; 1 min., 70° C.); 15 cycles (15 sec., 95° C.; 1 min., 70° C.). The amplification product is purified on a Sephadex G50 column.

The migration of the amplification product obtained in the column eluate is performed in denaturing gel (7M urea) of acrylamide of Long Ranger type (6%), in 1×TBE, on an Applied Biosystems 377 machine. The electrophoresis is carried out for 12 hours under 1500 V.

The preparation of the stock solution of nucleotides representing in this case a mixture of the four natural nucleoside triphosphates, depleted in thymidine triphosphate (known as dTTP mix) is carried out in the following way.

2 µL of a 1.25 mM solution of dTTP (Promega) are mixed with 2 µL of 5 mM dATP (Promega), 2 µL of 5 mM dCTP (Promega) and 2 µL of 5 mM dGTP (Promega).

TABLE 4

|  | 200 µM Morpholino T glycine | 500 µM Morpholino T glycine |
|---|---|---|
| TACS buffer (×5) | 2 µL | 2 µL |
| Z1M13 Primer (JOE) | 1 µL | 1 µL |
| DTTP mix | 1 µL | 1 µL |
| 2 mM Morpholino T glycine | 1 µL | 2.5 µL |
| Taq (3 U/µL) | 1 µL | 1 µL |
| Template | 1 µL | 1 µL |
| H$_2$O | 3 µL | 1.5 µL |

TABLE 5

|  | ddTTP 250 µM | ddTTP 300 µM |
|---|---|---|
| TACS buffer (×5) | 2 µL | 2 µL |
| Z1M13 Primer (ROX) | 1 µL | 1 µL |
| DTTP mix | 1 µL | 1 µL |
| 2.5 mM DdTTP | 1 µL | 2.5 µL |
| Taq (3 U/µL) | 1 µL | 1 µL |
| Template | 1 µL | 1 µL |
| H$_2$O | 3 µL | 1.5 µL |

The products of the sequencing reactions are detected by fluorescence. The results obtained are represented in the attached figure which illustrates the detection of the products in the sequencing gel analysed by the Perkin-Elmer Analysis software, version 3.0.

For each test, the primers are identifiable by their fluorescence properties, the ROX label (red) for the control reaction 250 µm dideoxythymidine triphosphate (dashed-curve) and the label JOE (green) for the reaction concerning the 200 µm morpholino T glycine (solid-line curve).

As shown in the figure, the results of these tests are entirely conclusive since the morpholino T glycine is correctly incorporated in a base-specific manner by the Taq polymerase, and acts correctly as a chain terminator.

The other three morpholino-nucleotides 1, 5 and 6 may be used in the same manner to determine the positions of the four DNA bases in the fragment to be analysed.

EXAMPLE 14

Testing Morpholino A Putrescine and Morpholino A Fluorescein in Sequencing

Morpholino A putrescine (MATPP) 7 and morpholino A fluorescein (MATPPF) 12 are tested in squencing reaction with fluorescent primers (Applied Biosystems, Perkin-Elmer, Foster City, Calif., USA) on a standard template which is a Bluescript plasmid DNA (Stratagene, La Jolla, Calif., USA). The enzyme used is a Taq polyerase (Perkin-Elmer) which is used in its buffer (Thermo Sequenase buffer, Amersham Life Science).

Three sequencing reactions are carried out with MATPP at 100, 200 and 400 µM and four sequencing reactions are carried out with MATPPF at 200, 500, 1000 and 5000 µM, along with control reactions with the dideoxynucleotide ddATP at a concentration of 250 µM (Boehringer).

The reaction medium, of a total volume of 10 µL, contains 125 ng of template, 1.25 pmol of fluorescent primer and the other constituents as described in the tables.

The medium is subjected to heating cycles in order to produce in number molecules of newly formed DNA strands. An amplification on a Perkin-Elmer 9700 machine (Gene Amp®, PCR System 9700) is carried out, according to the following sequences:

MATPP 7 3 min, 95° C.; 30 cycles (15 sec., 95° C.; 15 sec., 55° C.; 1 min, 70° C.)

MATPPF 12 3 min, 95° C.; 30 cycles (15 sec., 95° C.; 15 sec., 55° C.; 4 min, 60° C.)

The amplification products are purified on a Sephadex G50 column. The products of each sequencing reaction are mixed with the products of a control reaction and analysed by electrophoresis.

The migration of the mixture obtained is carried out in denaturing gel (7M urea) of acrylamide of Long Ranger type (6%), in 1× TBE, on an Applied Biosystems 377 machine (ABI Prism DNA Sequencer, Perkin-Elmer). The electrophoresis is carried out for 7 hours under 1680 V, 50 mA.

Preparation of the Stock Solution of Nucleotides: dATP Mix for 16 Reactions

[lacuna] representing in this case a mixture of the four natural nucleotide triphosphates, depleted in deoxyadenosine triphosphate (referred to as dATP mix): 4 µL of a 1.25 mM solution of dATP (Promega) are mixed with 4 µL of 5 mM dTTP (Promega), 4 µL of 5 mM dCTP(Promega) and 4 µL 5 mM dGTP (Promega).

TABLE 6

Preparation of the common mix for 15 reactions

|  | /reaction | /15 reactions |
|---|---|---|
| TACS buffer (×5) | 2 µL | 30 µL |
| dATP mix | 1 µL | 15 µL |
| Taq (5 U/µL) | 1 µL | 15 µL |
| Template (Bluescript plasmid) | 2 µL | 30 µL |

Preparation of the 2 mM Stock Solution of MATPP 7:
1.17 mg of MATPP 7 are diluted in 1.04 mL of H$_2$O.

TABLE 7

Reactions with 2 mM morpholino ATPP

|  | 400 µM Morpholino ATPP | 200 µM Morpholino ATTP | 100 µM Morpholino ATTP |
|---|---|---|---|
| Common mix | 6 µL | 6 µL | 6 µL |
| Z1M13 Primer (JOE) | 1 µL | 1 µL | 1 µL |
| 2 mM Morpholino ATPP | 2 µL | 1 µL | 0.5 µL |
| H$_2$O | 1 µL | 2 µL | 2.5 µL |

TABLE 8

Three control reactions with 2.5 mM dideoxyadenosine triphosphate (ddATP)

|  | 250 µM ddATP |
|---|---|
| Common mix | 6 µL |
| Z1M13 Primer (ROX) | 1 µL |
| 2.5 mM ddATP | 1 µL |
| H$_2$O | 2 µL |

Preparation of the 20 mM and 2 mM Stock Solutions of MATPPF 12

Solution S$_0$ at 20 mM: dilute the sample (2.2 mg) in 110.5 µL of H$_2$O

Solution S$_1$ at 2 mM: take 10 µL of S$_0$ and add 90 µL of H$_2$O

TABLE 9

Reactions with 20 mM morpholino ATPPF (S$_0$)

|  | 1000 µM MATPPF | 5000 µM MATTPF |
|---|---|---|
| Common mix | 6 µL | 6 µL |
| Z1M13 Primer (JOE) | 1 µL | 1 µL |
| 20 mM Morpholino ATPPF | 0.5 µL | 2.5 µL |
| H$_2$O | 2.5 µL | 0.5 µL |

TABLE 10

Reactions with 2 mM morpholino ATPPF 2 mM (S$_1$)

|  | 500 µM MATPPF | 200 µM MATTPF |
|---|---|---|
| Common mix | 6 µL | 6 µL |
| Z1M13 Primer (JOE) | 1 µL | 1 µL |
| 2 mM Morpholino ATPPF | 2.5 µL | 1 µL |
| H$_2$O | 0.5 µL | 2 µL |

TABLE 11

Four control reactions with 2.5 mM dideoxyadenosine triphosphate (ddATP)

|  | ddATP 250 µM |
|---|---|
| Common mix | 6 µL |
| Z1M13 Primer (ROX) | 1 µL |
| 2.5 mM ddATP | 1 µL |
| H$_2$O | 2 µL |

Figure 2:
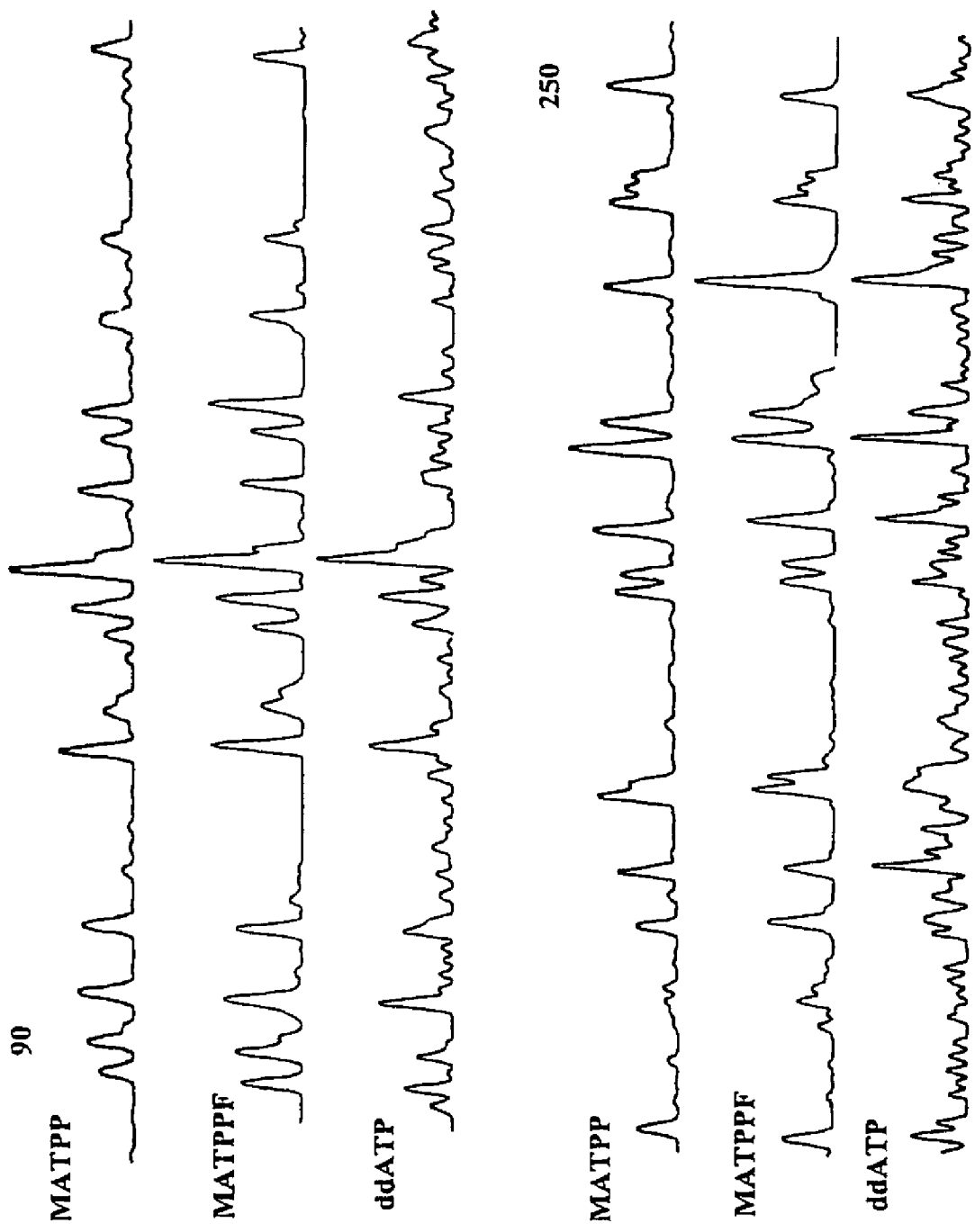
FIG. 2 is a diagram illustrating the results obtained by testing morpholino A putrescine (MATPP) and morpholino A fluorescein (MATPPF) in sequencing.

The results obtained with morpholino A putrescine 7 at 100 µM and morpholino A fluorescein 12 at 5 mM, between the 90th and the 250th base, are given in FIG. 2.

It is thus found that these two derivatives do indeed act as chain terminators. Furthermore, it should be noted that the reactions carried out with the fluorescent derivative, morpholino A fluorescein, were detected by means of the fluorophore borne by this derivative: a fluorescent chain terminator was thus prepared.

EXAMPLE 15

Use of Morpholino A Putrescine (MATPP) and Morpholino A Fluorescein (MATPPF) for the Template-Dependent 3' Labelling of DNA Fragments; Test of Enzymatic Incorporation of These Compounds by Three Polymerases (Taq, Klenow, Klenow Exo Free) and a Reverse Transcriptase These two nucleoside triphosphate derivatives are tested in enzymatic incorporation to label an oligonucleotide 13 bases long at its 3' end. This labelling is referred to as "template-dependent" since the enzymes used need the complementary strand to extend the oligonucleotide according to the Watson & Crick rules. Sequende A (17870 pmol/mL) studied and also its complementary target C (16128 pmol/mL) are given in the figure below:

```
Target C:   3'-TGC CAA CCA ACC CCA CCT CAA CCT CTG-5'
            (SEQ ID NO: 7)

Primer A:   5'-ACG GTT GGT TGG G (13 bp)
            (SEQ ID NO: 8)

Expected    5'-ACG GTT TGG GGT GGA (18 bp)
fragments   (SEQ ID NO: 9)
and         5'-ACG GTT GGT TGG GGT GGA GTT GGA
lengths     (24 bp) (SEQ ID NO: 10)
(bp):       5'-ACG GTT GGT TGG GGT GGA GTT GGA GA
            (26 bp) (SEQ ID NO: 11)
            5'-ACG GTT GGT TGG GGT GGA GTT GGA GAC
            (27 bp) (SEQ ID NO: 12)
```

Three enzymes are used for this labelling: Taq DNA polymerase (Boehringer Mannheim), the Klenow fragment (Boehringer Mannheim) and the Klenow exonuclease-free polymerase (Amersham Life Science). The primer is labelled at its 5' end by incorporation of $^{32}$P phosphate with the "Ready to go" T4 Polynucleotide Kinase kit (Pharmacia Biotech). The radiolabelled primer is noted A*.

The reaction buffers for the three enzymes are prepared for 10 reactions:

TABLE 12

| (in µL) | Taq reaction | Klenow Exo Free reaction |
|---|---|---|
| C | 50 | 50 |
| A | 10 | 10 |
| A* | 10 | 10 |
| Tp 10× | 50 | 50 |
| H$_2$O | 50 | 50 |

TABLE 13

| (in µL) | Klenow reaction |
|---|---|
| C | 50 |
| A | 10 |
| A* | 10 |
| Tp 5× | 100 |
| H$_2$O | 0 |

The enzymes are then diluted in the following manner, for 10 reactions:

Taq (5 U/µL): 10×0.1 µL of Taq+10×15.5 µL of H$_2$O

Klenow (20 U/µL): 10×0.1 µL of Klenow+10×15.5 µL of H$_2$O

Klenow Exo Free (5 U/µL): 10×0.1 µL of Klenow Exo Free+10×15.5 µL of H₂O.

Solutions containing the normal nucleoside triphosphates are also prepared:
Solution "2P" composed of a mixture of dGTP and dTTP each at 0.1 mM
Solution "4P" composed of a mixture of dATP, dCTP, dGTP and dTTP each at 0.1 mM The implementation reactions are described in Table 14 below:

TABLE 14

|  | 1 | 2<br>400 µM | 3<br>200 µM | 4<br>50 µM | 5<br>2.5 mM | 6<br>400 µM | 7<br>200 µM | 8<br>50 µM | 9 |
|---|---|---|---|---|---|---|---|---|---|
| Reaction | 17 | 17 | 17 | 17 | 17 | 17 | 17 | 17 | 17 |
| "2P" | 0 | 5 | 5 | 5 | 5 | 5 | 5 | 5 | 0 |
| "4P" | 0 | 0 | 0 | 0 | 0 | 0 | 0 | 0 | 5 |
| 2 mM MATPP | 0 | 10 | 5 | 1.25 | 0 | 0 | 0 | 0 | 0 |
| 20 mM MATPPF | 0 | 0 | 0 | 0 | 6.25 | 0 | 0 | 0 | 0 |
| 2 mM MATPPF | 0 | 0 | 0 | 0 | 0 | 10 | 5 | 1.25 | 0 |
| H₂O | 33 | 2.7 | 7.4 | 11.15 | 6.15 | 2.4 | 7.4 | 11.15 | 12.4 |
| Enzyme | 0 | 15.6 | 15.6 | 15.6 | 15.6 | 15.6 | 15.6 | 15.6 | 15.6 |

The morpholino A putrescine is thus tested at three concentrations: 400, 200 and 50 µM, while the morpholino A fluorescein is reacted at 2.5 mM, 400, 200 and 50 µM.

Before adding the enzyme, the mixture is denatured at 94° C. for 5 minutes. It is then left to return to ambient temperature in order for the hybridization to take place. The elongation is carried out at 70° C. for the Taq and at 37° C. for the two Klenow fragments, and for 10 minutes. Finally, the medium is again denatured with a formamide solution and heating at 90° C. for 5 minutes, after which it is placed on a polyacrylamide gel. The separation is carried out by electrophoresis at 2000 V. The gel is read using a Phosphorimager; the results obtained are given in FIG. 4.

In this figure, the lanes 1 serve as migration control for the labelled oligonucleotide A. This oligonucleotide has a length of 13 bases (13-mer). Lanes 2, 3 and 4 allow the elongation of the oligonucleotide A and the incorporation of the morpholino A putrescine to be monitored. Under these conditions, only the nucleotides dGTP and dTTP (solution "2P") were added and can be used by the enzyme to carry out the extention of the primer. The presence of the morpholino A putrescine in the reaction medium allows its incorporation at the level of base 18. A control was carried out, placing in the medium only the "2P" mixture; in this case, the enzyme continues its extension up to the 17th base since it has no adenosine derivative to continue its polymerization. Thus, the difference in migration between this control, which is 17 bases long, and reactions 2, 3 and 4 confirms the incorporation of MATPP and the interruption of the elongation of the chain. Reactions 5 to 8 correspond to the same reactions with morpholino A fluorescein. Here also, the MATPPF is indeed incorporated and stops the polymerization of the complementary strand. It is noted, however, for the two Klenow fragments, that there was occasionally incorporation of another base (G or T) in place of the morpholino derivative. Specifically, in these cases, elongation products corresponding to the 18-mer and 24-mer are found.

Well 9 (see FIG. 4) is a control reaction: the reaction medium contains the 4 normal deoxynucleotides and can consequently extend the primer up to its maximum extension, that is to say until the 27-mer is obtained.

In conclusion, the three enzymes incorporate the morpholino A putrescine and morpholino A fluorescein in all the concentrations tested, including the weakest concentrations.

The capacity of the reverse transciptases to incorporate the morpholino nucleotide derivatives in the course of the extension of oligonucleotides was confirmed. In this test, the reverse transcriptase (M-MLV, Promega; activity: 200,000 U/mL) is chosen as model. This enzyme is capable of synthesizing a DNA strand complementary to a target strand (DNA or RNA), from an oligonucleotide primer, in the presence of nucleoside triphosphates. Morpholino A putrescine and morpholino A fluorescein are thus tested at final concentrations of 250 µM. A control copy is also deposited on the gel, with the four nucleoside triphosphates of the "4P" solution.

The sequence of the target C (27-mer, 16128 pmol/mL) and that of the primer B (14-mer, 56368 pmol/mL) are shown below. This primer B, which is radioactively labelled, is noted B*.

The solution B* thus contains 10 pmol of primer B in a volume of 50 µL. The solutions of C and B are also diluted tenfold; these solutions are noted, respectively, C/10 and B/10.

```
Target C:
                                        (SEQ ID NO: 7)
3'-TGC AAC CCA ACC CCA CCT CAA CCT CTG-5'

Primer B:
                                       (SEQ ID NO: 13)
5'-ACG GTT GGT TGG GG (14 bp)
```

TABLE 15

| (in µL) | Reaction 1 | Reaction 2 | Reaction 3 | Reaction 4 |
|---|---|---|---|---|
| C/10 | 2 | 2 | 2 | 0 |
| B* | 5 | 5 | 5 | 5 |
| B/10 | 3 | 3 | 3 | 0 |
| 5× Buffer | 4 | 4 | 4 | 0 |
| 2 mM MATPP | 2.5 | 0 | 0 | 0 |
| 2 mM MATPPF | 0 | 2.5 | 0 | 0 |
| "2P" | 2.5 | 2.5 | 0 | 0 |
| "4P" | 0 | 0 | 2.5 | 0 |
| H₂O | 0 | 0 | 0 | 15 |
| Enzyme | 1 | 1 | 1 | 0 |

As previously, the mixture is denatured, before adding the enzyme, at 94° C. for 5 minutes and is left to cool to ambient temperature. The elongation is carried out at 37° C. for 60 minutes. The medium is denatured with a formamide solution and heating at 90° C. for 5 minutes before being deposited on a polyacrylamide gel. The separation is carried out by electrophoresis at 1500 V. The gel is read using a Phosphorimager; the results obtained are given FIG. 3.

In conclusion, the morpholino derivatives are very well recognized by reverse transcriptase and incorporated into the primers during extension in a base-specific process.

REFERENCES CITED

[1]: Sanger et al., Proceedings of National Academy of Science, 74, 1977, p. 5463-5467.
[2]: WO-A-96/23807.
[3]: Prober et al., Science, 238, 1987, pages 336-341.
[4]: Hileman et al., Bioconjugate Chemistry, 5, 1994, pages 436-444.
[5]: Broker et al., Nucleic acids Research, 5, 1978, pages 363-385.
[6]: Agrawal et al., Nucleic Acids Research, 14, 1986, pages 6227-6245.
[7]: FR-A-2 710 068
[8]: Rayford et al., Journal of Biological Chemistry, 260, 1985, pages 15708-15713.

That which is claimed is:

1. Process for manufacturing a morpholino-nucleotide of formula (I):

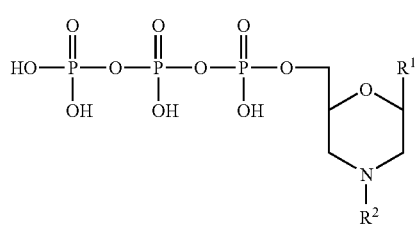

in which $R^1$ represents a nucleic base and $R^2$ is selected from the group consisting of:

—$(CH_2)_n$—NH—$R^3$—$(CH_2)_n$—$SR^3$

—$(CH_2)_n$—CO—$R^3$ and

—$(CH_2)_n$—$OR^3$ in which n is an integer ranging from 1 to 12 and $R^3$ is selected from the group consisting of a label, a protein, an enzyme, a fatty acid, and a peptide,
said process comprising
a) reacting a nucleoside triphosphate of formula (II):

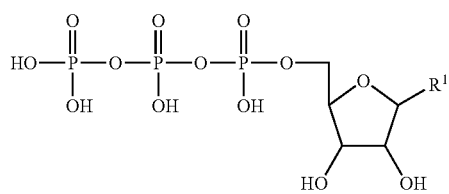

with a periodate, a compound of formula $R^{2'}NH_2$, wherein $R^{2'}$ is selected from the group consisting of:

—$(CH_2)_n$—$NH_2$—$(CH_2)_n$—SH

—$(CH_2)_n$—COOH and

—$(CH_2)_n$—OH, and sodium borohydride to form a morpholino-nucleotide of formula (III):

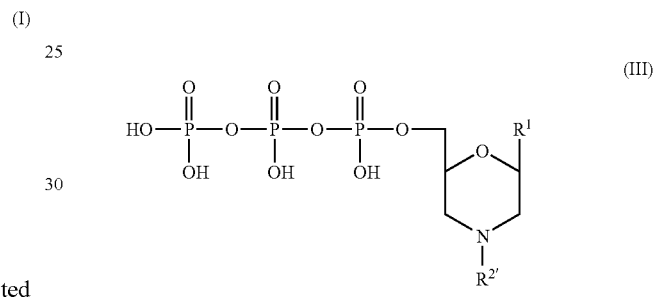

b) isolating the morpholino-nucleotide of formula (III); and c) attaching $R^3$ to the morpholino-nucleotide of formula (III) to form the morpholino-nucleotide of formula (I).

2. Process according to claim 1, in which $R^2$ is —$(CH_2)_n$—NH—$R^3$ and $R^3$ is fluorescein.

3. Process according to claim 2, wherein n is 4.

4. Process according to claim 1, wherein $R^3$ is a fluorophore.

5. Process for manufacturing a morpholino-nucleotide of formula (I):

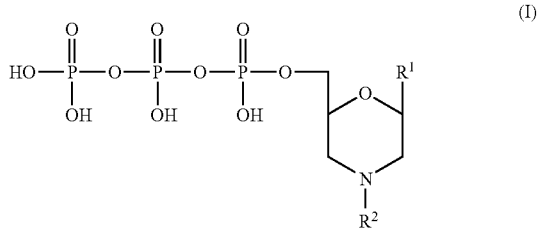

in which $R^1$ represents a nucleic base and $R^2$ is selected from the group consisting of:

—$(CH_2)_n$—$NH_2$—$(CH_2)_n$—SH

—$(CH_2)_n$—COOH—$(CH_2)_n$—OH

—$(CH_2)_n$—NH—$R^3$—$(CH_2)_n$—$SR^3$

—$(CH_2)_n$—CO—$R^3$ and

—$(CH_2)_n$—$OR^3$ in which n is an integer ranging from 1 to 12 and $R^3$ is selected from the group consisting of a label, a protein, an enzyme, a fatty acid, and a peptide, said process comprising reacting a nucleoside triphosphate of formula (II):

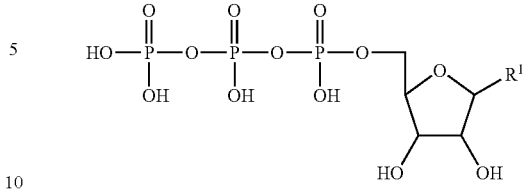

with a periodate, a compound of formula $R^2NH^2$, and sodium borohydride to form the morpholino-nucleotide of formula (I).

6. Process according to claim 5, wherein $R^3$ is a fluorophore.

7. Process according to claim 5, in which $R^2$ is —$(CH_2)_n$—NH—$R^3$ and $R^3$ is fluorescein.

8. Process according to claim 7, wherein n is 4.

* * * * *

UNITED STATES PATENT AND TRADEMARK OFFICE
CERTIFICATE OF CORRECTION

PATENT NO. : 7,314,928 B2
APPLICATION NO. : 11/411505
DATED : January 1, 2008
INVENTOR(S) : Florence Marciacq et al.

It is certified that error appears in the above-identified patent and that said Letters Patent is hereby corrected as shown below:

Column 36, Line 12: that portion of the formula reading "$R^2NH^2$" should read --$R^2NH_2$--.

Signed and Sealed this

Eighth Day of July, 2008

JON W. DUDAS
*Director of the United States Patent and Trademark Office*